United States Patent
Kiely et al.

(10) Patent No.: US 11,529,381 B2
(45) Date of Patent: *Dec. 20, 2022

(54) BIFIDOBACTERIUM LONGUM ABLE TO BENEFICIALLY MODULATE IMMUNE RESPONSE TO RESPIRATORY VIRUS INFECTION

(71) Applicant: PrecisionBiotics Group Limited, Cork (IE)

(72) Inventors: Barry Kiely, Cork (IE); Liam O'Mahony, Cork (IE); David Groeger, Cork (IE)

(73) Assignee: PrecisionBiotics Group Limited, Cork (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/489,141

(22) PCT Filed: Feb. 28, 2018

(86) PCT No.: PCT/EP2018/054914
§ 371 (c)(1),
(2) Date: Aug. 27, 2019

(87) PCT Pub. No.: WO2018/158306
PCT Pub. Date: Sep. 7, 2018

(65) Prior Publication Data
US 2020/0000859 A1 Jan. 2, 2020

(30) Foreign Application Priority Data
Feb. 28, 2017 (EP) .................................. 17158564
Feb. 28, 2017 (EP) .................................. 17158567

(51) Int. Cl.
| | | |
|---|---|---|
| *A61K 35/745* | (2015.01) | |
| *A61K 9/00* | (2006.01) | |
| *A23L 33/135* | (2016.01) | |
| *A61P 31/16* | (2006.01) | |
| *C12N 1/20* | (2006.01) | |
| *C12R 1/01* | (2006.01) | |

(52) U.S. Cl.
CPC .......... *A61K 35/745* (2013.01); *A23L 33/135* (2016.08); *A61K 9/0043* (2013.01); *A61P 31/16* (2018.01); *C12N 1/205* (2021.05); *A23V 2002/00* (2013.01); *A23Y 2300/55* (2013.01); *C12R 2001/01* (2021.05)

(58) Field of Classification Search
None
See application file for complete search history.

(56) References Cited

U.S. PATENT DOCUMENTS

| | | |
|---|---|---|
| 4,157,278 A | 6/1979 | Ross et al. |
| 4,464,362 A | 8/1984 | Kludas et al. |
| 2003/0092163 A1* | 5/2003 | Collins .................. A61P 25/00 435/252.1 |
| 2009/0196921 A1* | 8/2009 | Ebel ........................ A61P 37/04 424/457 |
| 2009/0230013 A1* | 9/2009 | Born ...................... A61J 7/0084 206/531 |
| 2010/0278793 A1 | 11/2010 | Gueniche et al. |
| 2011/0020284 A1 | 1/2011 | MacSharry et al. |
| 2011/0020400 A1 | 1/2011 | MacSharry et al. |
| 2011/0046084 A1 | 2/2011 | Grant et al. |
| 2012/0201798 A1 | 8/2012 | Kekkonen et al. |
| 2012/0230956 A1 | 9/2012 | McLean et al. |
| 2013/0165470 A1* | 6/2013 | Isfort .................... A61K 9/0043 514/289 |
| 2013/0180524 A1 | 7/2013 | Shahaf et al. |
| 2013/0224253 A1 | 8/2013 | Petit et al. |
| 2015/0044188 A1 | 2/2015 | Griffiths |
| 2016/0106937 A1 | 4/2016 | Shahaf et al. |
| 2016/0250265 A1 | 9/2016 | Petit et al. |
| 2017/0128678 A1 | 5/2017 | Shahaf et al. |
| 2018/0177834 A1 | 6/2018 | Griffiths |

FOREIGN PATENT DOCUMENTS

| | | |
|---|---|---|
| AU | 2010288546 B2 | 8/2015 |
| CN | 1433811 A | 8/2003 |
| CN | 102321187 A | 1/2012 |
| EP | 2181703 A1 | 5/2010 |
| EP | 2455092 A1 | 5/2012 |
| JP | 2005-508617 A | 4/2005 |
| JP | 2007169200 A | 7/2007 |
| JP | 2010-522552 A | 7/2010 |
| JP | 2010-522553 A | 7/2010 |
| JP | 2013-507431 A | 3/2013 |

(Continued)

OTHER PUBLICATIONS

Almond M. H., et al. "Obesity and Susceptibility to Severe Outcomes Following Respiratory Viral Infection", *Thorax*. Jul. 2013, 68 (7); pp. 684-686. doi: 10.1136/thoraxjnl-2012-203009.

Amrouche T., et al., "Effects of Bifidobacterial Cytoplasm, Cell Wall and Exopolysaccharide on Mouse Lymphocyte Proliferation and Cytokine Production", *International Dairy Journal*, 2006, 16; pp. 70-80.

Bartlett N. W., et al., "Mouse Models of Rhinovirus Infection and Airways Disease", *Methods in Molecular Biology.*, 2015;1221, pp. 181-188. doi: 10.1007/978-1-4939-1571-2_14.

Bouhnik Y., "Survie et Effets Chez L'homme des Bacteries Ingérées Dans Les Laits Fermentés", *Lait* 1993, 73, pp. 241-247.

(Continued)

*Primary Examiner* — Olivia M. Wise
*Assistant Examiner* — Sharon M. Papciak
(74) *Attorney, Agent, or Firm* — Bookoff McAndrews, PLLC

(57) ABSTRACT

An isolated strain of *Bifidobacterium longum* NCIMB 42020 is useful for the treatment of viral infections, especially viral respiratory infections such as influenza, rhinovirus and RSV. *Bifidobacterium longum* NCIMB 42020 is also useful for clearing secondary bacterial infections.

9 Claims, 20 Drawing Sheets

Specification includes a Sequence Listing.

(56) References Cited

FOREIGN PATENT DOCUMENTS

| | | |
|---|---|---|
| JP | 2017-081853 A | 5/2017 |
| RU | 2151606 C1 | 6/2000 |
| RU | 2216588 C1 | 1/2004 |
| RU | 2314341 C1 | 1/2008 |
| RU | 255731 C2 | 12/2013 |
| WO | WO 2008/053444 A2 | 5/2008 |
| WO | WO 2012/029064 A1 | 3/2012 |
| WO | WO 2012/062780 A1 | 5/2012 |
| WO | WO 2015/021530 A1 | 2/2015 |
| WO | WO 2015/140299 A1 | 9/2015 |
| WO | WO 2016/009377 A1 | 1/2016 |
| WO | WO 2016/120320 A1 | 8/2016 |
| WO | WO 2016/142767 A1 | 9/2016 |
| WO | WO 2017/032897 A1 | 3/2017 |
| WO | WO 2018/047106 A1 | 3/2018 |
| WO | WO 2018/158309 A1 | 9/2018 |
| WO | WO 2018/168449 A1 | 9/2018 |

OTHER PUBLICATIONS

Davidson S., et al., "Pathogenic Potential of Interferon $\alpha\beta$ in Acute Influenza Infection", *Nature Communications*, May 21, 2014; 5:3864, pp. 1-15.

Davidson S., et al., "IFN$\lambda$ Is a Potent Anti-Influenza Therapeutic Without the Inflammatory Side Effects of IFN$\alpha$ treatment", *EMBO Molecular Medicine.*, Sep. 1, 2016 ;8(9):pp. 1099-1112.

Durbin R. K., et al., "Interferon Induction and Function at the Muscol Surface", *Immunol Rev.* Sep. 2013; 255(1): pp. 25-39.

Galani I.E., et al., "Interferon-$\lambda$ Mediates Non-Redundant Front-Line Antiviral Protection Against Influenza Virus Infection Without Compromising Host Fitness", *Immunity*, May 16, 2017; 46(5): pp. 875-890.

Groeger D., et al., "*Bifidobacterium infantis* 35624 Modulates Host Inflammatory Processes Beyond the Gut", *Gut Microbes*, Jul.-Aug. 2013; 4(4): pp. 325-339. doi: 10.4161/gmic.25487.

Hartshorn K.L., et al., "Mechanisms of Anti-influenza Activity of Surfactant Proteins A and D: Comparison With Serum Collectins", *American Journal of Physiological Society*, 1997; 273: L1156-L1166.

Hartshorn K.L., et al., "Mechanism of Binding of Surfactant Protein D to Influenza A Viruses: Importance of Binding to Haemagglutinin to Antiviral Activity", *Biochem J* 2000; 351 (Pt 2): pp. 449-458.

Hawgood S. et al., "Pulmonary Collectins Modulate Strain-Specific Influenza A Virus Infection and Host Responses", Journal of Virology, 2004; 78: pp. 8565-8572.

Hewitt R., et al., "The Role of Viral Infections in Exacerbations of Chronic Obstructive Pulmonary Disease and Asthma", Therapeutic Advances in Respiratory Disease, Apr. 2016;10(2): pp. 158-174. doi: 10.1177/1753465815618113.

Homayouni A. R., et al., "Can Probiotics Prevent or Improve Common Cold and Influenza?", *Nutrition* 2019, 29; pp. 805-806.

Ichikawa A., et al., "CXCL10-CXCR3 Enhances the Development of Neutrophil-Mediated Fulminant Lung Injury of Viral and Nonviral Origin", American Journal of Respiratory and Critical Care Medicine, Jan. 1, 2013;187(1): pp. 65-77.

Ivashkiv L. B., et al., "Regulation of Type I Interferon Responses", *Nat Rev Immunol*, Jan. 2014; 14(1): pp. 36-49.

Iwabuchi, N., et al., "Effects of Intranasal Administration of *Bifidobacterium longum* BB536 on Mucosal Immune System in Respiratory Tract and Influenza Virus Infection in Mice", *Milk Science*,2009, vol. 58, No. 3; pp. 129-133.

Iwabuchi N., et al., "Oral Administration of *Bifidobacterium longum* Ameliorates Influenza Virus Infection in Mice", *Biol. Pharm. Bull* , 2011. 34(8) pp. 1352-1355.

Jartti T., et al., "Role of Viral Infections in the Development and Exacerbation of Asthma in Children", *J Allergy Clin Immunol*. Oct. 2017;140(4): pp. 895-906.

Jounblat R., et al., "The Role of Surfactant Protein D in the Colonisation of the Respiratory Tract and Onset of Bacteraemia During Pneumococcal Pneumonia", *Respiratory Research*, Oct. 28, 2005;6:126, pp. 1-12.

Kawahara T., et al., "Consecutive Oral Administration of *Bifidobacterium longum* MM-2 Improves the Defense System Against Influenza Virus Infection by Enhancing Natural Killer Cell Activity in a Murine Model", Microbiology and Immunology, 2015: 59: pp. 1-12.

Konieczna P., et al., "*Bifidobacterium linfantis* 35624 Administration Includes Foxp3 T Regulatory Cells in Human Peripheral Blood: Potential Role for Myeloid and Plasmacytoid Dendritic Cells", *Gut Microbiota*, Mar. 2012;61(3): pp. 354-366. doi: 10.1136/gutjnl-2011-300936.

Lazear H. M., et al., "Interferon-$\lambda$ Immune Functions at Barrier Surfaces and Beyond", *Immunity*, Jul. 21, 2015;43(1): pp. 15-28.

Lei, W., et al., "Effect of Probiotics and Prebiotics on Immune Response to Influenza Vaccination in Adults: A Systematic Review and Meta-Analysis of Randomized Controlled Trials", *Nutrients*, 2017, 9, 1175, pp. 1-17.

Levine A. M., et al., "Surfactant Protein D Enhances Clearance of Influenza A Virus From the Lung in In Vivo Mouse Models", *The Journal of Immunology*, 2001; 167: pp. 5868-5873.

Levine A. M., et al., "Surfactant Protein-D Enhances Phagocytosis and Pulmonary Clearance of Respiratory Syncytial Virus", *American Journal of Respiratory Cell and Molecular Biology*, Aug. 2004;31(2): pp. 193-199.

Li W., et al., "Type I Interferon Induction During Influenza Virus Infection Increases Susceptibility to Secondary *Streptococcus pneumoniae* Infection by Negative Regulation of Gammadelta T Cells", *Journal of Virology*, 2012; 86:pp. 12304-12312.

Mendoza J. L. et al., "The IFN-$\lambda$-IFN-$\lambda$R1-IL-10R$\beta$ Complex Reveals Structural Features Underlying Type III IFN Functional Plasticity", *Immunity*, Mar. 21, 2017;46(3): pp. 379-392.

Molenkamp G.C., et al., "Effects of Antibiotics on Metabolism of Peptidoglycan, Protein, and Lipids in *Bifidobacterium bifidum* subsp. *pennsulvanicus"*, *Antimicrobial Agents and Chemotherapy*, vol. 10, No. 5, (Nov. 1, 1976), pp. 786-794, XP55461829.

Nakamura S. et al., "Synergistic Stimulation of Type I Interferons During Influenza Virus Coinfection Promotes *Streptococcus pneumoniae* Colonization in Mice", *The Journal of Clinical Investigation* 2011;121: pp. 3657-3665.

Namba K., et al. "Effects of *Bifidobacterium longum* BB536 Administration of Influenza Infection, Influenza Vaccine Antibody Titer, and Cell-Mediated Immunity in the Elderly", *Biosci. Biotechnol. Biochem* 2010. 74, pp. 939-945.

O'Mahony C., et al., "Commensal-Induced Regulatory T Cells Mediate Protection Against Pathogen-Stimulated NF-kB Activation", *PLOS Pathogens*, Aug. 2008, vol. 4, Issue 8, pp. 1-10.

O'Mahony L., et al., "*Lactobacillus* and *Bifidobacterium* in Irritable Bowel Syndrome: Symptom Responses and Relationship to Cytokine Profiles", *Gastroenterology*. Mar. 2005;128(3): pp. 541-551.

Reading P.C., et al., "Collectin-Mediated Antiviral Host Defense of the Lung: Evidence From Influenza Virus Infection of Mice", *Journal of Virology*, Nov. 1997;71: pp. 8204-8212.

Rich H., et al., "The Role of Interferon Lambda During Influenza, *Staphylococcus aureus* Super-Infection", *The Journal of Immunology*, May 1, 2017, 198(1 Supplement) 77.16.

Sastry K., et al., "Collectins: Pattern Recognition Molecules Involved in First Line Host Defense", *Current Opinion in Immunology*, 5: pp. 59-66, 1993.

Schiavi E., et al., "The Surface-Associated Exopolysaccharide of *Bifidobacterium longum* 35624 Plays an Essential Role in Dampening Host Proinflammatory Responses and Repressing Local $T_H17$ Responses", *Applied and Environmental Microbiology*, vol. 82, No. 24, Dec. 15, 2016; pp. 7185-7196.

Sekine K., et al., "A New Morphologically Characterized Cell Wall Preparation (Whole Peptidoglycan) From *Bifidobacterium infantis* With a Higher Efficacy on the Regression of an Established Tumor in Mice", *Cancer Research, AACR—American Association for Cancer Research*, US, vol. 45, No. 3, Jan. 1, 1985; pp. 1300-1307.

(56) References Cited

OTHER PUBLICATIONS

Shahangian A. et al., "Type I IFNs Mediate Development of Postinfluenza Bacterial Pneumonia in Mice", *The Journal of Clinical Investigation*, 2009;119: pp. 1910-1920.
Shi X., et al., "Inhibition of the Inflammatory Cytokine Tumor Necrosis Factor-Alpha With Etanercept Provides Protection Against Lethal H1N1 Influenza Infection in Mice", *Critical Care*, 2013; 17(6);R301, pp. 1-9.
Steinke J. W., et al., "Immune Responses in Rhinovirus-Induced Asthma Exacerbations", *Curr Allergy Asthma Rep*. Nov. 2016;16(11):78, pp. 1-14.
Tecle T., et al., "Inhibition of Influenza Viral Neuraminidase Activity by Collectins", *Archives of Virology* 2007; 152: pp. 1731-1742.
Thiel S., et al., "Structures and Functions Associated With the Group of Mammalian Lectins Containing Collagen-Like Sequences", *FEBS Letter 07262*, Jun. 1989, vol. 250, No. 1, pp. 78-84.
Vigerust D.J., et al., "N-Linked Glycosylation Attenuates H3N2 Influenza Viruses", *Journal of Virology*, 2007; 81: pp. 8593-8600.
Wack A., et al., "Guarding the Frontiers: The Biology of the Type III Interferons", *Nature Immunology*. Jul. 2015, 16(8): pp. 802-809.
Wang W., et al., "Monoclonal Antibody Against CXCL-10/IP-10 Ameliorates Influenza A (H1N1) Virus Induced Acute Lung Injury", *Cell Research* (2013) 23: pp. 577-580.
World Health Organization 2007. "Global Surveillance, Prevention and Control of Chronic Respiratory Diseases, A Comprehensive Approach", (Editors Jean Bousquet and Nikolai Khaltaev), pp. 1-155.
Yang J. W., et al., "Corticosteroids for the Treatment of Human Infection With Influenza Virus: A Systematic Review and Meta-Analysis", *Clinical Microbiology and Infection*, Oct. 2015; 21(10): pp. 956-963.
Yeh, T., et al., "The Influence of Prebiotic and Probiotic Supplementation on Antibody Titers After Influenza Vaccination: A Systematic Review and Meta-Analysis of Randomized Controlled Trials", *Drug Design, Development and Therapy*, Jan. 2018:12; pp. 217-230.
Zeleya H., et al., "Respiratory Antiviral Immunity and Immunobiotics: Beneficial Effects on Inflammation-Coagulation Interaction During Influenza Virus Infection", *Frontiers in Immunology*, Dec. 2016, vol. 7, Article 633.
Zhou X., et al., "Exacerbation of Chronic Obstructive Pulmonary Disease", *Cell Biochem Biophys*, Nov. 2015; 73(2): pp. 349-355.
International Search Report for PCT/EP2018/054914, dated Apr. 17, 2018 (3 pages).
Lopez, P. et al., "Distinct *Bifidobacterium* Strains Drive Different Immune Responses In Vitro," *International Journal of Food Microbiology*, 138, pp. 157-165 (2010).
Medina, M. et al., "Differential Immunomodulatory Properties of Bifidobacterium logum Strains: Relevance to Probiotic Selection and Clinical Applications," *Clinical and Experimental Immunology*, vol. 150, pp. 531-538 (2007).
Allen, AP, et al., "*Bifidobacterium longum* 714 as a Translational Psychobiotic: Modulation of Stress, Electrophysiology and Neurocognition in Healthy Volunteers", *Translational Psychiatry*, 2016, vol. 6, pp. 1-6.
Channappanavar, R., et al., "Dysregulated Type I Interferon and Inflammatory Monocyte-Macrophase Responses Cause Lethal Pneumonia in SARS-CoV-Infected Mice", *Cell Host & Microbe*, 2016, vol. 19, pp. 181-193.
Chasset, F., et al., Type I Interferons in Systems Autoimmune Diseases: Distinguishing Between Afferent and Efferent Functions for Precision Medicine and Individualized Treatment, *Frontiers in Pharmacology*, 2021, vol. 1, pp. 1-18.
Cole, S. L., et al., "Contribution of Innate Immune Cells to Pathogenesis of Severe Influenza Virus Infection", *Clinical Science*, 2017, vol. 131, 269-83.
Davidson, S.A., "Unique and Overlapping Actions of Type I and III IFNs in Influenza A Virus Infection and Implications for Therapy", 2016, The Open University.
Dunning, J., et al., "Seasonal and Pandemic Influenza: 100 Year of Progress, Still Much to Learn", *Mucosal Immunology*, 2020, vol. 13, pp. 566-573.
Holvoet, S., et al., "Characterization of Candidate Anti-Allergic Probiotic Strains in a Model of Th2-Skewed Human Peripheral Blood Mononuclear Cells", *Int Arch Allergy Immunol*, 2013, vol. 161, pp. 142-154.
Iwabuchi, N., et al., "Immuno-modulating effects of *Bifidobacterium longum* BB536 and the mechanisms", *Milk Science*, 2010, vol. 59, No. 3; pp. 275-281.
Iwabuchi, N., et al., "Suppressive Effects of *Bifidobacterium longum* on the Production of Th2-attracting Chemokines Induced with T Cell-Antigen-Presenting Cell Interactions", *FEMS Immunol Med Microbiol*, 2009, vol. 55, pp. 324-334.
Monticelli, L.A., et al., "Innate Lymphoid Cells Promote Lung-Tissue Homeostasis After Infection with Influenza Virus", *Nature Immunology*, 2011, vol. 12, No. 11, pp. 1045-1056.
Pegram, H.J., et al. "Activating and Inhibitory Receptors of Natural Killer Cells", Immunology and Cell Biology, 2011, vol. 89, 216-24.
Sun, J., "Effector T Cells Control Lung Inflammation During Acute Influenza Virus Infection by Producing IL-10", *Nature Medicine*, 2009, vol. 15, No. 3, pp. 277-284.

\* cited by examiner

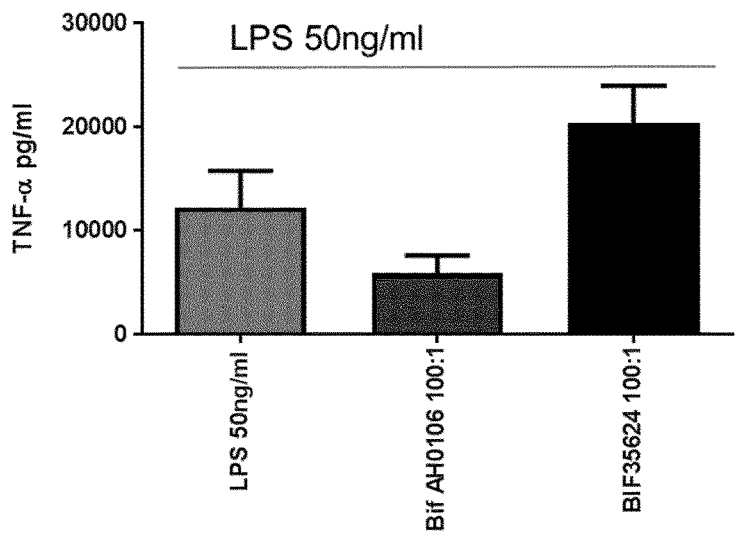
Fig. 9
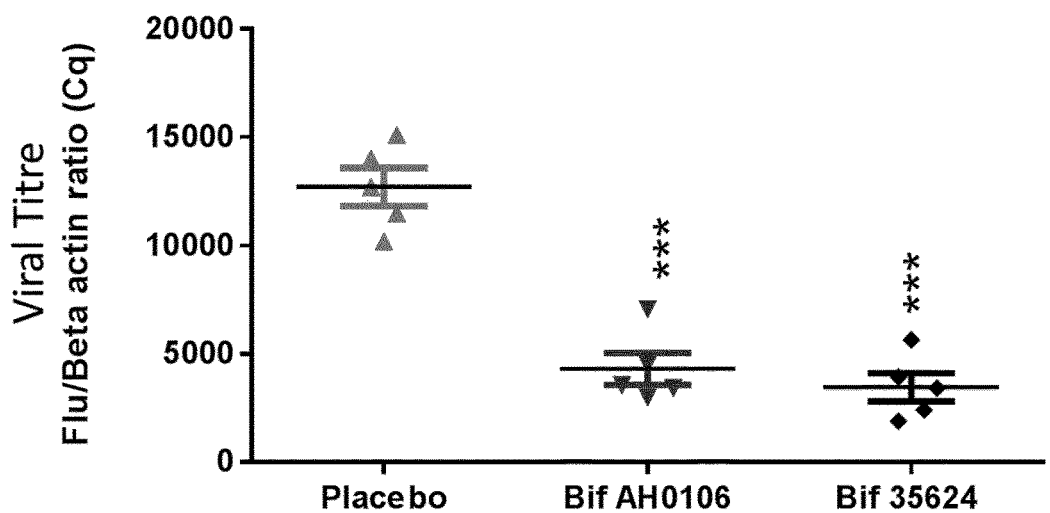
Fig. 10
| % Survival /Days | | | | | |
|---|---|---|---|---|---|
| | Days 1-6 | Day 7 | Days 8 | Days 9 | Days 10 |
| Placebo | 100 | 40 | 40 | 20 | 0 |
| Bif AH0106 | 100 | 60 | 60 | 60 | 60 |
| Bif 35624 | 100 | 60 | 40 | 20 | 20 |
Fig. 11

SEQUENCE LISTING

<160> NUMBER OF SEQ ID NOS: 5

<210> SEQ ID NO 1
<211> LENGTH: 18
<212> TYPE: DNA
<213> ORGANISM: Bifidobacterium longum

<400> SEQUENCE: 1
ctggtgccaa ggcatcca                                                    18

<210> SEQ ID NO 2
<211> LENGTH: 19
<212> TYPE: DNA
<213> ORGANISM: Bifidobacterium longum

<400> SEQUENCE: 2
gctggatcac ctcctttct                                                   19

<210> SEQ ID NO 3
<211> LENGTH: 498
<212> TYPE: DNA
<213> ORGANISM: Bifidobacterium longum

<400> SEQUENCE: 3
ttgctgggat cacctccttt ttacggagaa ttcagtcgga tgttcgtccg acggtgtgcg      60
ccccgcgcgt cgcatggtgc gatggcggcg gggttgctgg tgtggaaaac gtcgttggct     120
ttgccctgcc ggtcgtgcgg tgggtgcggg gtggtatgga tgcgcttttg ggctcccgga     180
tcgccacccc aggcttttg cctggcgcga ttcgatgccc gtcgtgcctg ggggccggcc      240
gtgtgccggc gcgatggcgt ggcggtgcgt ggtggcttga gaactggata gtggacgcga     300
gcaaaacaag ggttttgaa tctttgtttt gctgttgatt tcgaatcgaa ctctattgtt      360
cgtttcgatc gttttgtgat catttttagt gtgatgattt gtcgtcctgg gaatttgcta     420
gaggaatact tgcgggccat gcactttcgt ggtgtgtgtt gcttgcaagg gcgtatggtg     480
gaggccttgg caccagaa                                                   498

<210> SEQ ID NO 4
<211> LENGTH: 20
<212> TYPE: DNA
<213> ORGANISM: Bifidobacterium longum

<400> SEQUENCE: 4
ggactgcagc gtagacgctt                                                  20

<210> SEQ ID NO 5
<211> LENGTH: 21
<212> TYPE: DNA
<213> ORGANISM: Bifidobacterium longum

<400> SEQUENCE: 5
catcctgtat atgaggccca t                                                21

BIFIDOBACTERIUM LONGUM ABLE TO BENEFICIALLY MODULATE IMMUNE RESPONSE TO RESPIRATORY VIRUS INFECTION

CROSS-REFERENCE TO RELATED APPLICATIONS

This application is the U.S. national phase entry under 35 U.S.C. § 371 of International Application No. PCT/EP2018/054914, filed on Feb. 28, 2018, which claims benefit to European Patent Application Nos. 17158564.9 and 17158567.2, both filed on Feb. 28, 2017.

SEQUENCE LISTING

This application contains a sequence listing, submitted electronically in ASCII format under the file name 00175-0007-00000_SL.txt, which is incorporated by reference herein in its entirety. The ASCII copy of the sequence listing was created on Aug. 24, 2019, and is 1,803 bytes in size.

FIELD OF THE INVENTION

The invention relates to Bifidobacteria which are one of several predominant culturable bacteria present in human colonic microflora.

BACKGROUND OF THE INVENTION

Bifidobacteria are considered to be probiotics as they are living organisms which exert healthy effects beyond basic nutrition when ingested in sufficient numbers. A high level of ingested bifidobacteria must reach their site of action in order to exert a probiotic effect. A minimum level of approximately $10^6$-$10^7$ viable bifidobacteria per gram intestinal contents has been suggested (Bouhnik, Y, Lait 1993). There are reports in the literature which show that in vivo studies completed in adults and in infants indicate that some strains of bifidobacteria are capable of surviving passage through the gastrointestinal tract. Significant differences have been observed between the abilities of different bifidobacteria strains to tolerate acid and bile salts, indicating that survival is an important criterion for the selection of potential probiotic strains.

Ingestion of bifidobacteria can improve gastrointestinal transit and may prevent or assist in the treatment of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhoea, cardiovascular disease, and certain cancers (e.g. colorectal cancer).

Viral infections are a major cause of morbidity and mortality. Influenza virus, rhinovirus (common cold) and respiratory syncytial virus (RSV) are highly infectious viruses that usually are successfully cleared by an appropriate host immune response in healthy individuals. However much of the issue with these infections is not the initial virus but rather the secondary infections that often accompany it e.g. bacterial infections causing pneumonia, infection of sinus tissue etc. Susceptible individuals such as those suffering from COPD or Asthma or Obesity respond very poorly to viral infections and subsequent secondary infections are serious and can be life threatening to such individuals.

These virus-induced exacerbations of these conditions are associated with substantial healthcare costs and significant suffering. Development of new and effective therapies for these exacerbations would be beneficial as there is a major unmet clinical need. Administration of corticosteroids to patients affected by influenza virus, especially pandemic avian influenza virus, although relatively common, remains controversial. Routine steroid use is not be ideal for influenza virus infection as it does not reduce the viral burden and also inhibits the clearance of secondary bacterial infections afterwards (Yang et al, 2015).

In the early stages of infection, influenza, rhinovirus and RSV replication occurs in lung epithelial cells, leading to activation of viral sensors and the release of antiviral Type I and Type III interferons (IFN's) as well as chemokines and cytokines. These pro-inflammatory mediators help to clear the primary infection but Type I IFN's can also cause subsequent damage (immunopathology). IFN Type I responses, such as increases in IFN-α and IFN-β molecules, have been shown to directly correlate with increased morbidity and mortality in models of influenza infection (Davidson et al, 2014). Over-production of antiviral Type I IFN's and the related IP-10 chemokine inhibit the appropriate immune response to clear secondary infections (Nakamura et al, 2011; Shahangian et al, 2009; Li et al, 2012) such as caused by bacterial agents such as *Streptococcus pneumonia, Moraxella catarrhalis*, and *Haemophilus influenzae* and even *Staphylococcus aureus* (Hewitt et al, 2016). These secondary infections cause excessive cell death within the lungs. In susceptible individuals, this leads to lung tissue injury and reduced lung function which causes serious complications and mortality in some cases e.g. in COPD patients. Importantly the pro-inflammatory activation occurs only to Type I IFN responses which cause the recruitment of neutrophils and not to Type III IFN responses (Galani et al, 2017).

However, Type III IFN's such as IFN lambda (IFN-λ) can limit viral replication without inducing pro-inflammatory responses or immunopathology (Davidson et al, 2016; Galani et al, 2017).

Therefore, therapeutic agents that can limit the Type I IFN responses and accompanying pro-inflammatory and tissue damaging response to viral infection, while maintaining appropriate Type III responses and anti-viral defence, would be a significant advancement in the management of respiratory viral infections. This reduction of immunopathology is critical for host survival and resolution of disease.

Other innate sensors or immune mediators can also play an important role in early anti-viral defence Surfactant protein D (SP-D) can stop the influenza virus from entering epithelial cells which is part of the early phase of the infection. (Thiel et al, 1989; Sastry et al, 1993). Again, therapeutic agents that can induce this innate sensor which can bind to the virus and stop it from infecting the bronchial epithelial cells would be a significant advancement in the treatment of viruses such as influenza, rhinovirus and RSV. In addition, inhibition of tumor necrosis factor-alpha (TNF-α), an important inflammatory cytokine has a significant effect on the extent of lung immunopathology and inhibited inflammatory cellular infiltration and cytokine responses. TNF-α, has been shown to correlate with morbidity and mortality in macaques monkeys and humans infected with highly virulent influenza viruses. A decrease in influenza virus replication and an increased survival of influenza virus-infected mice was observed when the TNF-α was suppressed (Shi et al, 2013). Inhibition of this inflammatory cytokine with etanercept provides protection against lethal H1N1 influenza infection in mice (Shi et al, 2013).

Therapeutic agents which can induce Type III IFN-λ and/or SP-D would have a role to play in early clearance of the primary viral infection while reducing the likelihood of secondary bacterial infections and would be a significant advancement in the management of ARDS, asthma, obesity and COPD.

SUMMARY OF THE INVENTION

According to the invention there is provided a *Bifidobacterium longum* strain having the accession number NCIMB 42020. The strain of *Bifidobacterium longum* AH0106 was deposited with the NCIMB under accession number 42020, on Aug. 2, 2012, under the terms of the Budapest Treaty at the National Collections of Industrial and Marine Bacteria Limited (NCIMB) Ferguson Building, Craibstone Estate, Bucksburn, Aberdeen, AB21 9YA, Scotland, UK. The strain may be in the form of a biologically pure culture.

Also provided is an isolated strain of *Bifidobacterium longum* NCIMB 42020.

The strain may be in the form of viable cells and/or in the form of non-viable cells.

The strain the may be isolated from faeces or gastrointestinal tract of healthy human subjects.

The strain may be in the form of a bacterial broth. Alternatively, the strain is in the form of a freeze-dried powder.

The strain attenuates the IP-10 response to a virus. This is important because IP-10 is secreted by several cell types in response to IFN-γ. These cell types include monocytes and endothelial cells. IP-10 has been attributed to several roles, including chemoattraction for monocytes/macrophages, T cells, NK cells, and dendritic cells, and promotion of T cell adhesion to endothelial cells and is a marker of viral induced host system activation.

The strain may enhance the type III interferon response to a virus such as the interferon lambda response to a virus.

The strain may suppress the interferon type I response to a virus such as the interferon alpha response to a virus and/or the interferon beta response to a virus.

The strain may enhance the surfactant protein D response to a virus.

The invention also provides a formulation which comprises a *Bifidobacterium* strain of the invention.

The formulation may further comprise another probiotic material and/or a prebiotic material.

The formulation may further comprise an ingestable carrier. The ingestable carrier may be a pharmaceutically acceptable carrier such as a capsule, tablet or powder. The ingestable carrier may be a food product such as acidified milk, yoghurt, frozen yoghurt, ice-cream, milk powder, milk concentrate, ice cream, cheese spread, dressing or beverage.

The formulation may further comprise a protein and/or peptide, in particular proteins and/or peptides that are rich in glutamine/glutamate, a lipid, a carbohydrate, a vitamin, mineral and/or trace element.

The *Bifidobacterium* strain may be present in an amount of more than $10^6$ cfu per gram of the formulation.

The formulation may further comprise an adjuvant, a drug entity, and/or a biological compound.

The formulation may be adapted for administration to the lung or to the nose. For example, the formulation may be in the form of a nasal spray. The viscosity of the formulation may be from 1 cps to 2000 cps.

The *Bifidobacterium* strain or a formulation thereof may be for use in foodstuffs or for use as a medicament.

The *Bifidobacterium* strain or a formulation thereof may be for use in the prophylaxis and/or treatment of undesirable inflammatory activity.

The *Bifidobacterium* strain or an active derivative or fragment or mutant or variant thereof may be for use in the prophylaxis and/or treatment of undesirable inflammatory activity.

The *Bifidobacterium* strain or a formulation thereof may be for use in the preparation of a medicament for treating asthma and/or allergy, the medicament may be in a form suitable for inhalation.

The *Bifidobacterium* strain or a formulation thereof may be for use in the prophylaxis or treatment of a viral infection in a subject.

The *Bifidobacterium* strain or a formulation thereof may be for use in the prophylaxis of a secondary bacterial infection associated with a respiratory viral infection in a subject.

The virus in some cases is a respiratory virus which may be selected from influenza virus, rhinovirus, and respiratory syncytial virus.

The subject may have been diagnosed with an inflammatory lung disease.

In some cases the subject has increased susceptibility to a respiratory infection.

The subject may be one or more of obese, an acute respiratory distress syndrome (ARDS) patient, an asthma patient, or a chronic obstructive pulmonary disease (COPD) patient.

In one case the subject is a child less than 5 years of age.

In another case the subject is an elderly person greater than 60 years of age.

The invention also provides a method for prophylaxis or treatment of a viral infection in a subject comprising administering to a subject in need thereof, an effective amount of a strain of *Bifidobacterium longum* NCIMB 42020 or active derivative, or fragment or mutant or variant thereof.

The *Bifidobacterium longum* strain NCIMB 42020 or active derivative, or fragment or mutant or variant thereof may:
 attenuate the IP-10 response to a virus;
 enhance the type III interferon response to the virus such as the interferon lambda response to the virus;
 suppress the interferon type I response to the virus such as the interferon alpha response to the virus and/or the interferon beta response to the virus; and/or
 enhance the surfactant protein D response to the virus.

Also provided is a cell wall fraction isolated from *Bifidobacterium longum* strain NCIMB 42020.

The cell wall fraction may:
 attenuate the IP-10 response to a virus;
 enhance the type III interferon response to the virus such as the interferon lambda response to the virus;
 suppress the interferon type I response to the virus such as the interferon alpha response to the virus and/or the interferon beta response to the virus; and/or
 enhance the surfactant protein D response to the virus.

The virus in some cases is a respiratory virus which may be selected from influenza virus, rhinovirus, and respiratory syncytial virus.

The subject may have been diagnosed with an inflammatory lung disease.

In some cases the subject has increased susceptibility to a respiratory infection.

The subject may be one or more of obese, an acute respiratory distress syndrome (ARDS) patient, an asthma patient, or a chronic obstructive pulmonary disease (COPD) patient.

In one case the subject is a child less than 5 years of age.

In another case the subject is an elderly person greater than 60 years of age.

The cell wall fraction may have a molecular weight greater than 100 kDa. The cell wall fraction may be less than 0.45 μm in size.

In one embodiment the fraction is isolated by opening the *Bifidobacterium longum* and separating the cell wall fraction from a cytoplasmic fraction.

Also provided is a cell wall fraction isolated from the *Bifidobacterium longum* strain for use in the prophylaxis or treatment of a respiratory viral infection in a subject.

The invention also provides a cell wall fraction isolated from the *Bifidobacterium longum* strain for use in the prophylaxis of a secondary bacterial infection associated with a respiratory viral infection in a subject Also provided is a process for isolating a cell wall fraction of the *Bifidobacterium longum* comprising the steps of:—
  opening the *Bifidobacterium longum* to form a cell wall fraction and a cytoplasmic fraction; and
  separating the cell wall fraction from the cytoplasmic fraction.

The opening of the *Bifidobacterium longum* may comprise at least one of:—
  treating with a chelating agent;
  treating with an enzyme; and
  applying shear force.

The chelating agent may be a calcium chelating agent such as ethylenediaminetetraacetic acid (EDTA). The enzyme may be a glycoside hydrolase such as lysozyme. Alternatively or additionally the enzyme is a muralytic enzyme such as mutanolysin.

The shear force may be applied by sonication and/or by pressure such as by a French press.

The separation may comprise centrifugation.

In some cases, after separation, the cell wall fraction is filtered to provide a fraction with a size of less than 0.45 μm.

Also provided is a formulation which comprises the cell wall fraction.

The formulation may further comprise another probiotic material and/or a prebiotic material.

The formulation may further comprise an ingestable carrier. The ingestable carrier may be a pharmaceutically acceptable carrier such as a capsule, tablet or powder. The ingestable carrier may be a food product such as acidified milk, yoghurt, frozen yoghurt, ice-cream, milk powder, milk concentrate, ice cream, cheese spread, dressing or beverage.

The formulation may further comprise a protein and/or peptide, in particular proteins and/or peptides that are rich in glutamine/glutamate, a lipid, a carbohydrate, a vitamin, mineral and/or trace element.

The formulation may further comprise an adjuvant, a drug entity, and/or a biological compound.

The formulation may be adapted for administration to the lung or to the nose. For example, the formulation may be in the form of a nasal spray. The viscosity of the formulation may be from 1 cps to 2000 cps.

The invention provides an isolated strain of *Bifidobacterium longum* NCIMB 42020 (AH0106).

The invention also provides a mutant or variant of an isolated strain of *Bifidobacterium longum* NCIMB 42020.

The isolated strain may be in the form of viable cells.

The isolated strain may be in the form of non-viable cells.

The invention also provides a formulation comprising an isolated strain of *Bifidobacterium longum* NCIMB 42020.

The formulation may comprise an ingestible carrier. The ingestible carrier may be a pharmaceutically acceptable carrier such as a capsule, tablet or powder. The ingestible carrier may be a food product such as acidified milk, yoghurt, frozen yoghurt, milk powder, milk concentrate, cheese spreads, dressings or beverages.

In one embodiment the strain attenuates the IP-10 response to a virus.

In one embodiment the strain enhances the type III interferon response to the virus.

In one embodiment the strain suppresses the interferon alpha response to the virus.

In one embodiment the strain suppresses the interferon beta response to the virus.

In one case the strain:—
  attenuates the IP-10 response to the virus;
  enhances the type III interferon response to the virus;
  suppresses the interferon alpha response to the virus; and
  suppresses the interferon beta response to the virus.

The strain may be present at more than $10^6$ cfu per gram of ingestible carrier.

The invention further provides a composition comprising an isolated strain of *Bifidobacterium longum* NCIMB 42020 and a pharmaceutically acceptable carrier.

The invention also provides for the use of a *Bifidobacterium longum* strain NCIMB 42020 as a probiotic strain.

In one embodiment the formulation is adapted for administration to the lung or to the nose.

It will be appreciated that the specific strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

The invention also provides a *Bifidobacterium* strain of the invention or a formulation of the invention for use in the prophylaxis or treatment of a viral infection in a subject.

In one case the subject is an acute respiratory distress syndrome (ARDS) patient.

In another case the subject is an asthma patient.

In a further case the subject is a chronic obstructive pulmonary disease (COPD) patient.

The invention also provides a cell wall fraction isolated from *Bifidobacterium longum* NCIMB 42020 wherein the cell wall fraction attenuates the IP-10 response to a virus.

In one case the fraction enhances the type III interferon response to the virus.

In one case the fraction suppresses the interferon alpha response to the virus.

In one case the fraction suppresses the interferon beta response to the virus.

The invention further provides a cell wall fraction isolated from *Bifidobacterium longum* NCIMB 42020, wherein the cell wall fraction:—
- attenuates the IP-10 response to the virus;
- enhances the type III interferon response to the virus;
- suppresses the interferon alpha response to the virus; and
- suppresses the interferon beta response to the virus.

In one case the molecular weight of the cell wall fraction is greater than 100 kDa.

In one case the cell wall fraction is less than 0.45 m in size.

In one case the cell wall fraction has a molecular weight of greater than 100 kDa and is less than 0.45 µm in size.

The invention further provides a method for prophylaxis or treatment of a viral infection in a subject comprising the step of administering a cell wall fraction isolated from *Bifidobacterium longum* NCIMB 42020.

In one case the cell wall fraction attenuates the IP-10 response to a virus.

In one case the fraction enhances the type III interferon response to the virus.

In one case the fraction suppresses the interferon alpha response to the virus.

In one case the fraction suppresses the interferon beta response to the virus.

Also provided is a method for the prophylaxis or treatment of a viral infection in a subject comprising administering a cell wall fraction isolated from *Bifidobacterium longum* NCIMB 42020, wherein the fraction:—
- attenuates the IP-10 response to the virus;
- enhances the type III interferon response to the virus;
- suppresses the interferon alpha response to the virus; and
- suppresses the interferon beta response to the virus.

In one case the molecular weight of the cell wall fraction is greater than 100 kDa.

In one case the cell wall fraction is less than 0.45 µm in size.

In one case the cell wall fraction is administered in a formulation which is suitable for administration to the lung or the nose.

In one case the subject is an acute respiratory distress syndrome (ARDS) patient.

In one case the subject is an asthma patient.

In one case the subject is a chronic obstructive pulmonary disease (COPD) patient.

The invention also includes mutants and variants of the deposited strains. Throughout the specification the terms mutant, variant and genetically modified mutant include a strain whose genetic and/or phenotypic properties are altered compared to the parent strain. Naturally occurring variant includes the spontaneous alterations of targeted properties selectively isolated. Deliberate alteration of parent strain properties is accomplished by conventional (in vitro) genetic manipulation technologies, such as gene disruption, conjugative transfer, etc. Genetic modification includes introduction of exogenous and/or endogenous DNA sequences into the genome of a strain, for example, by insertion into the genome of the bacterial strain by vectors, including plasmid DNA, or bacteriophages.

Natural or induced mutations include at least single base alterations such as deletion, insertion, transversion or other DNA modifications which may result in alteration of the amino acid sequence encoded by the DNA sequence.

The terms mutant, variant and genetically modified mutant also include a strain that has undergone genetic alterations that accumulate in a genome at a rate which is consistent in nature for all micro-organisms and/or genetic alterations which occur through spontaneous mutation and/or acquisition of genes and/or loss of genes which is not achieved by deliberate (in vitro) manipulation of the genome but is achieved through the natural selection of variants and/or mutants that provide a selective advantage to support the survival of the bacterium when exposed to environmental pressures such as antibiotics. A mutant can be created by the deliberate (in vitro) insertion of specific genes into the genome which do not fundamentally alter the biochemical functionality of the organism but whose products can be used for identification or selection of the bacterium, for example, antibiotic resistance.

A person skilled in the art would appreciate that mutant or variant strains of can be identified by DNA sequence homology analysis with the parent strain. Strains of having a close sequence identity with the parent strain without demonstrable phenotypic or measurable functional differences are considered to be mutant or variant strains. A strain with a sequence identity (homology) of 99.5% or more with the parent DNA sequence may be considered to be a mutant or variant. Sequence homology may be determined using on-line homology algorithm "BLAST" program, publicly available at http://www.ncbi.nlm.nih.gov/BLAST/.

BRIEF DESCRIPTION OF THE DRAWINGS

The invention will be more clearly understood from the following description thereof given by way of example only with reference to the accompanying drawings in which;—

FIG. 9 is a bar chart of the TNF-α response to LPS in the presence of *B. longum* strains AH0106 and 35624;

FIG. 10 is a graph of viral replication in the lung in response to the strains *B. longum* AH0106, *B. longum* 35624 and placebo following viral infection;

FIG. 11 is a graph of survival over a time period post infection with the *B. longum* strains AH0106, 35624 and placebo;

DETAILED DESCRIPTION OF THE INVENTION

Figure 1A:
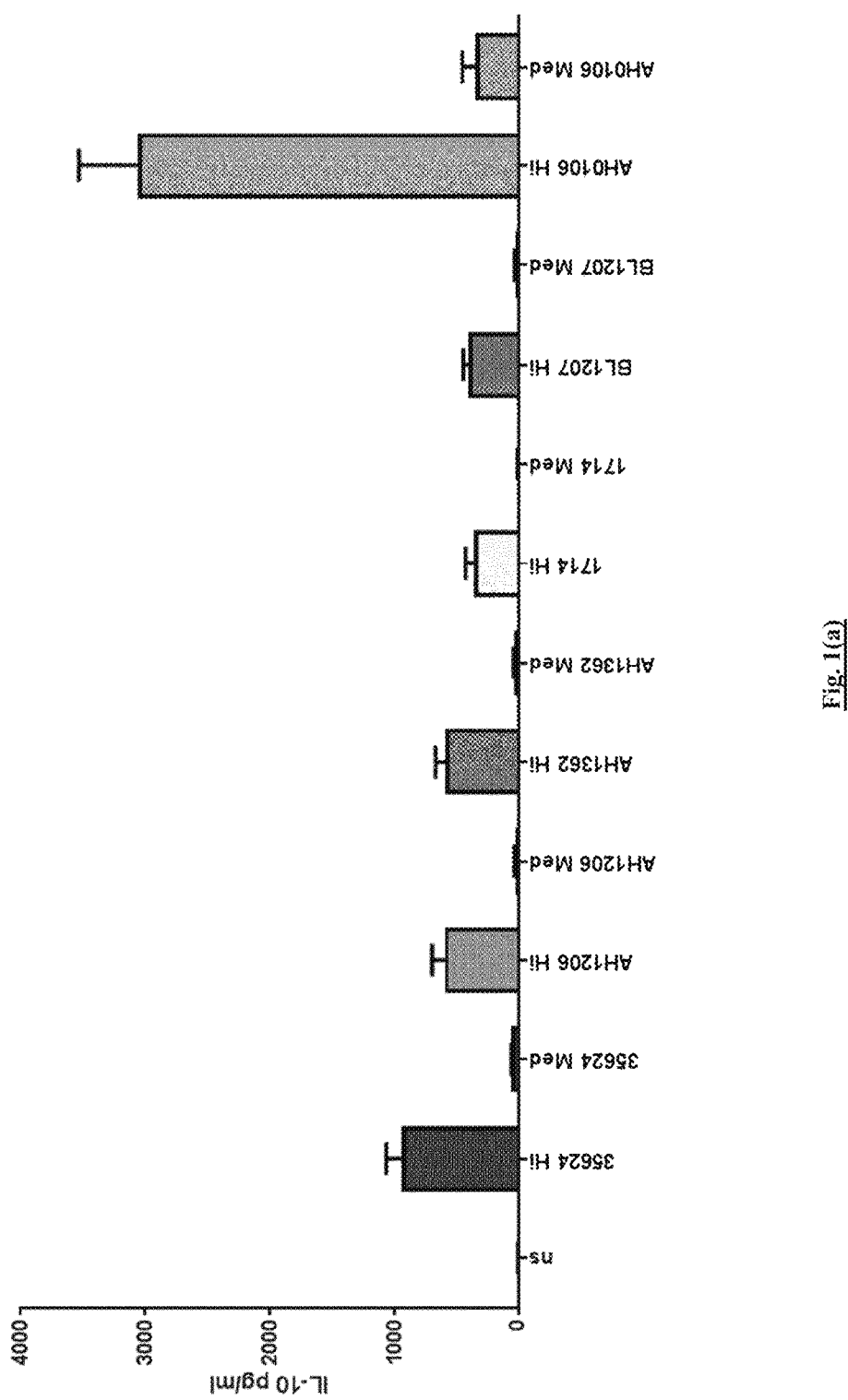
FIGS. 1(a) and 1(b) are bar graphs showing the induction profile of IL-10 in PBMC and in MDDCs after in vitro stimulation with increasing concentrations (medium and high) of *B. longum* strains 35624, AH1206, AH1362, 1714, BL1207 and AH0106.
Figure 1B:
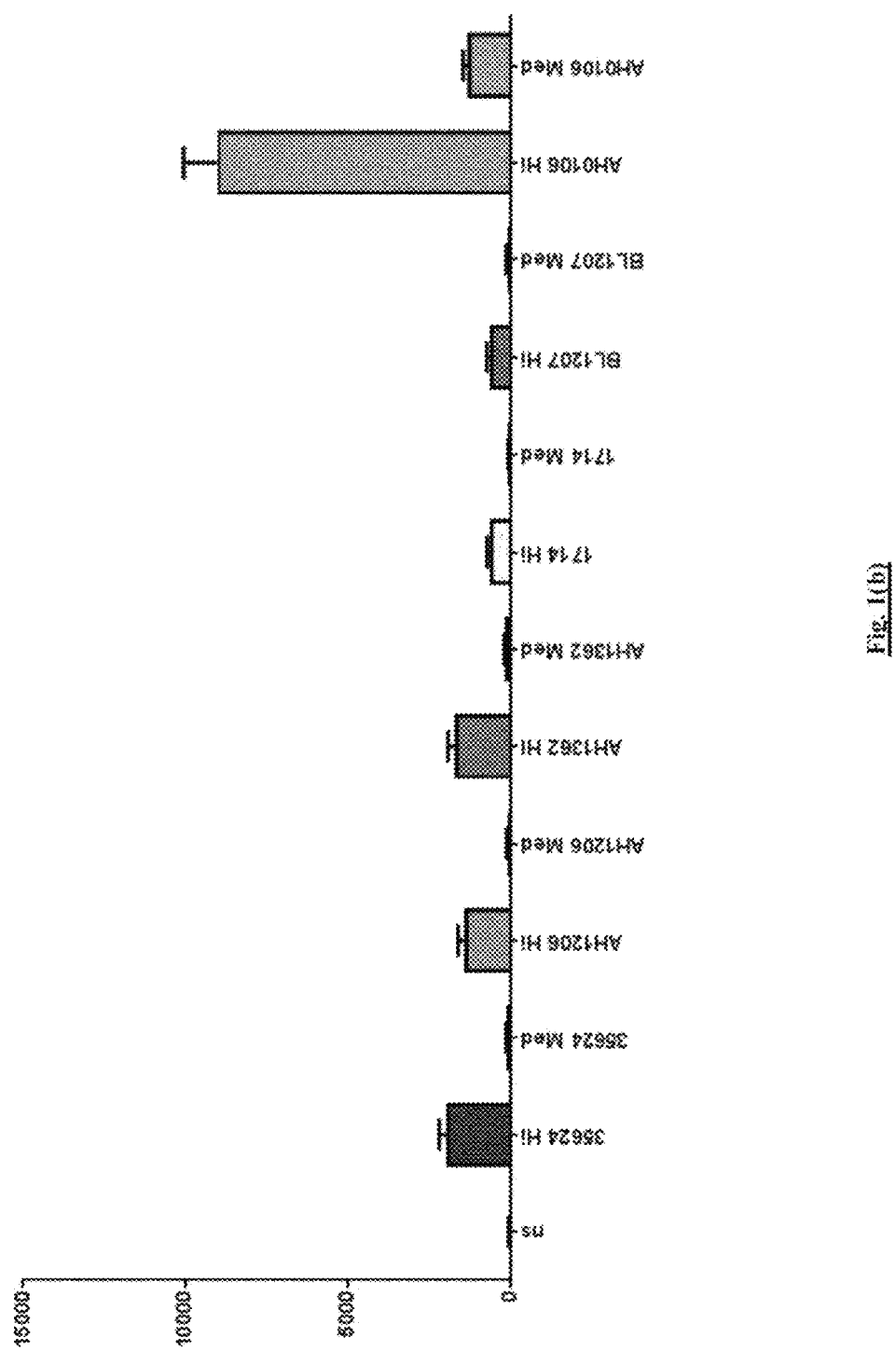
Figure 2A:
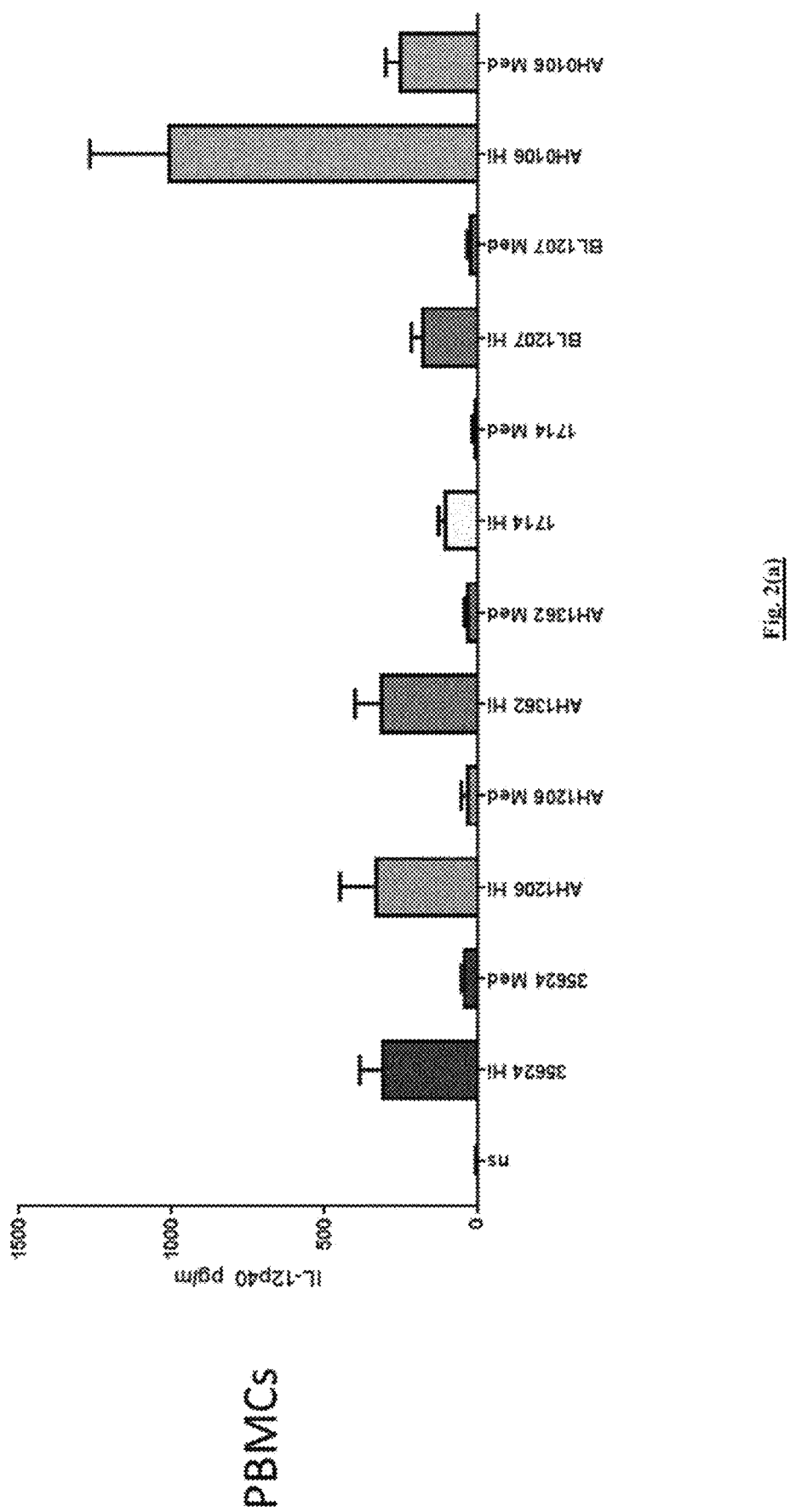
FIGS. 2(a) and 2(b) are bar graphs showing the induction profile of IL-12p40 in PBMC and in MDDCs after in vitro stimulation with increasing concentrations (medium and high) of *B. longum* strains 35624, AH1206, AH1362, 1714, BL1207 and AH0106.
Figure 2B:
Figure 3A:
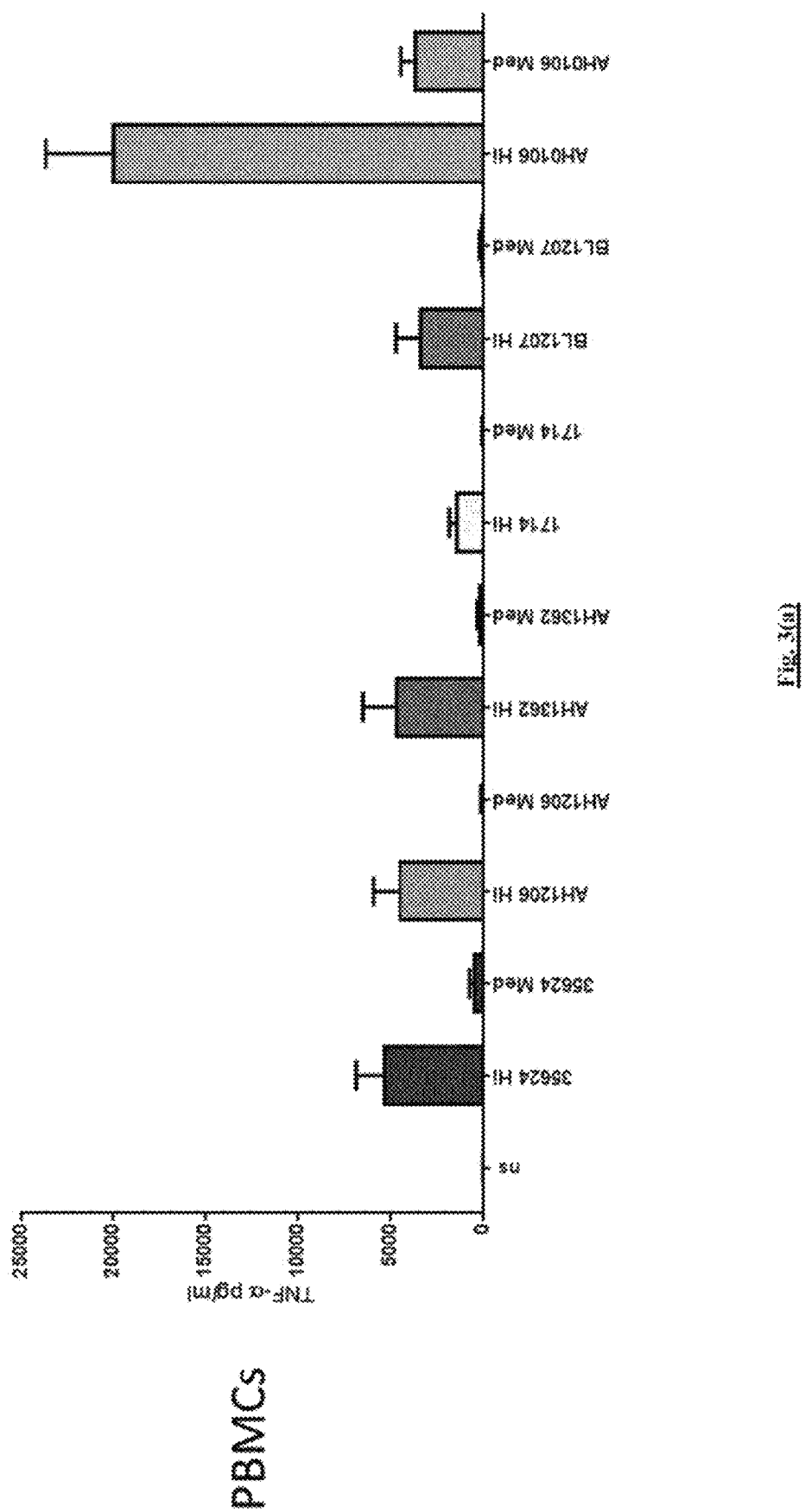
FIGS. 3(a) and 3(b) are bar graphs showing the induction profile of TNF-α in PBMC and in MDDCs after in vitro stimulation with increasing concentrations (medium and high) of *B. longum* strains 35624.
Figure 3B:
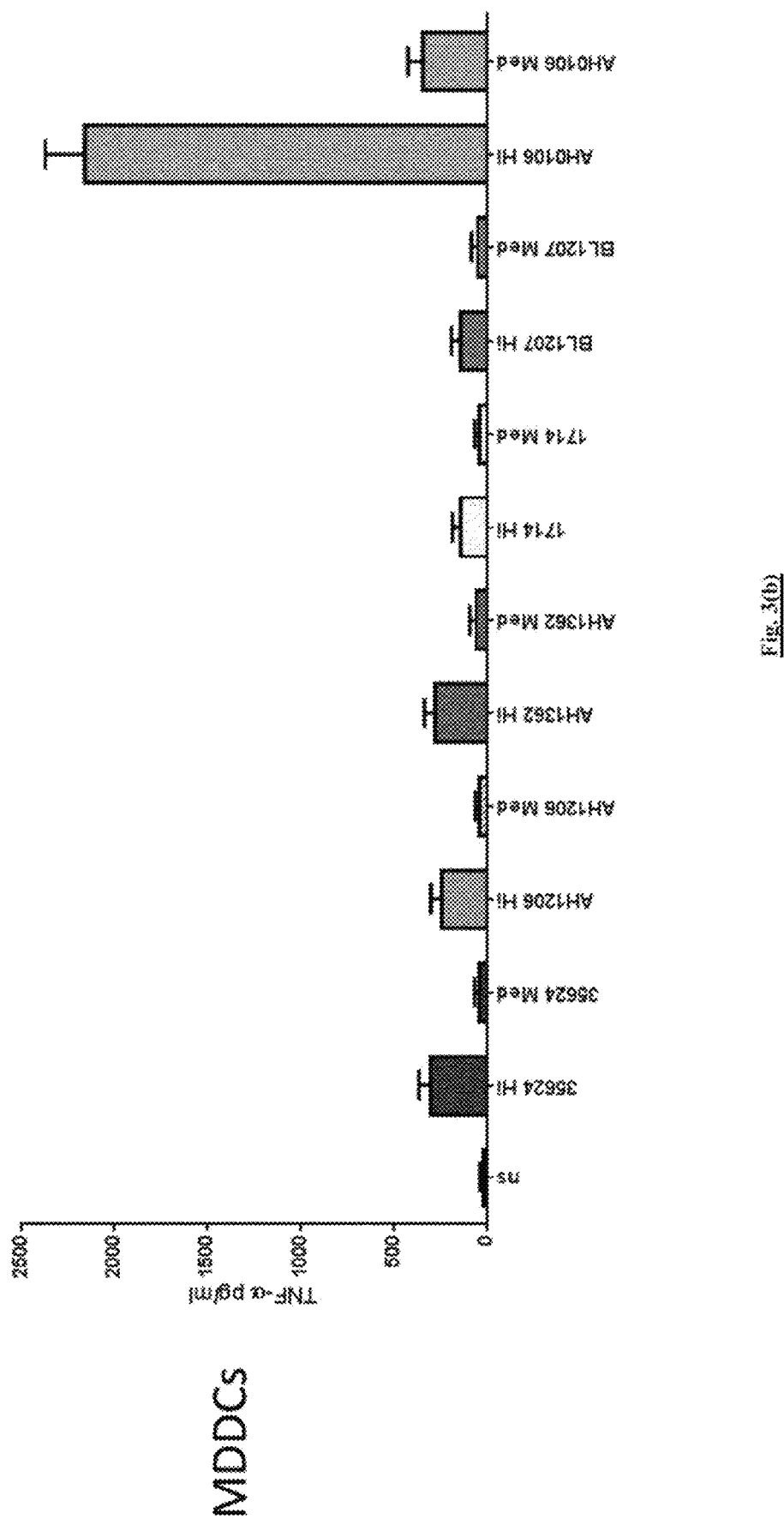
Figure 4A:
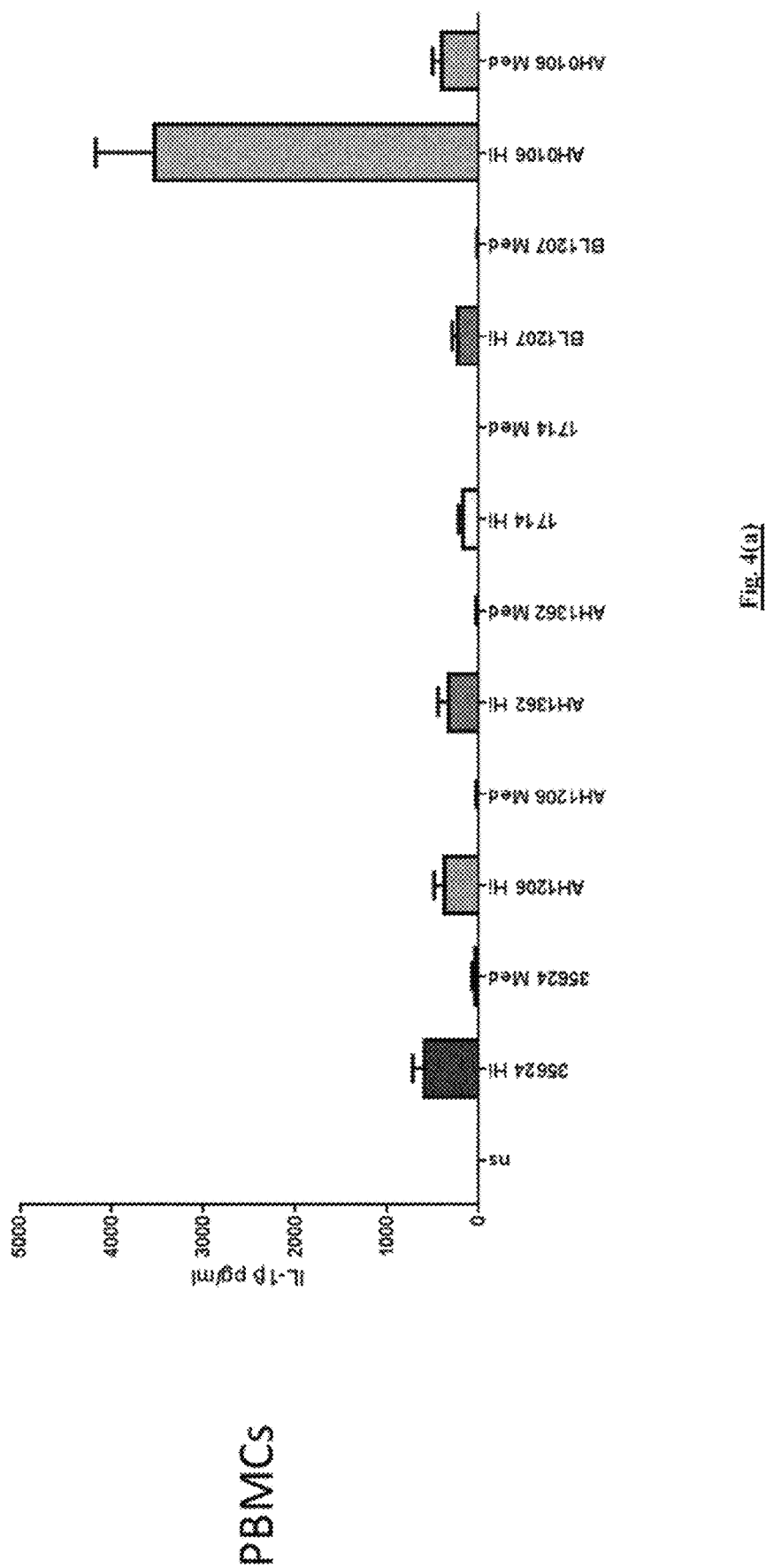
FIGS. 4(a) and 4(b) are bar graphs showing the induction profile of IL-0 in PBMC and in MDDCs after in vitro stimulation with increasing concentrations (medium and high) of *B. longum* strains 35624, AH1206, AH1362, 1714, BL1207 and AH0106.
Figure 4B:
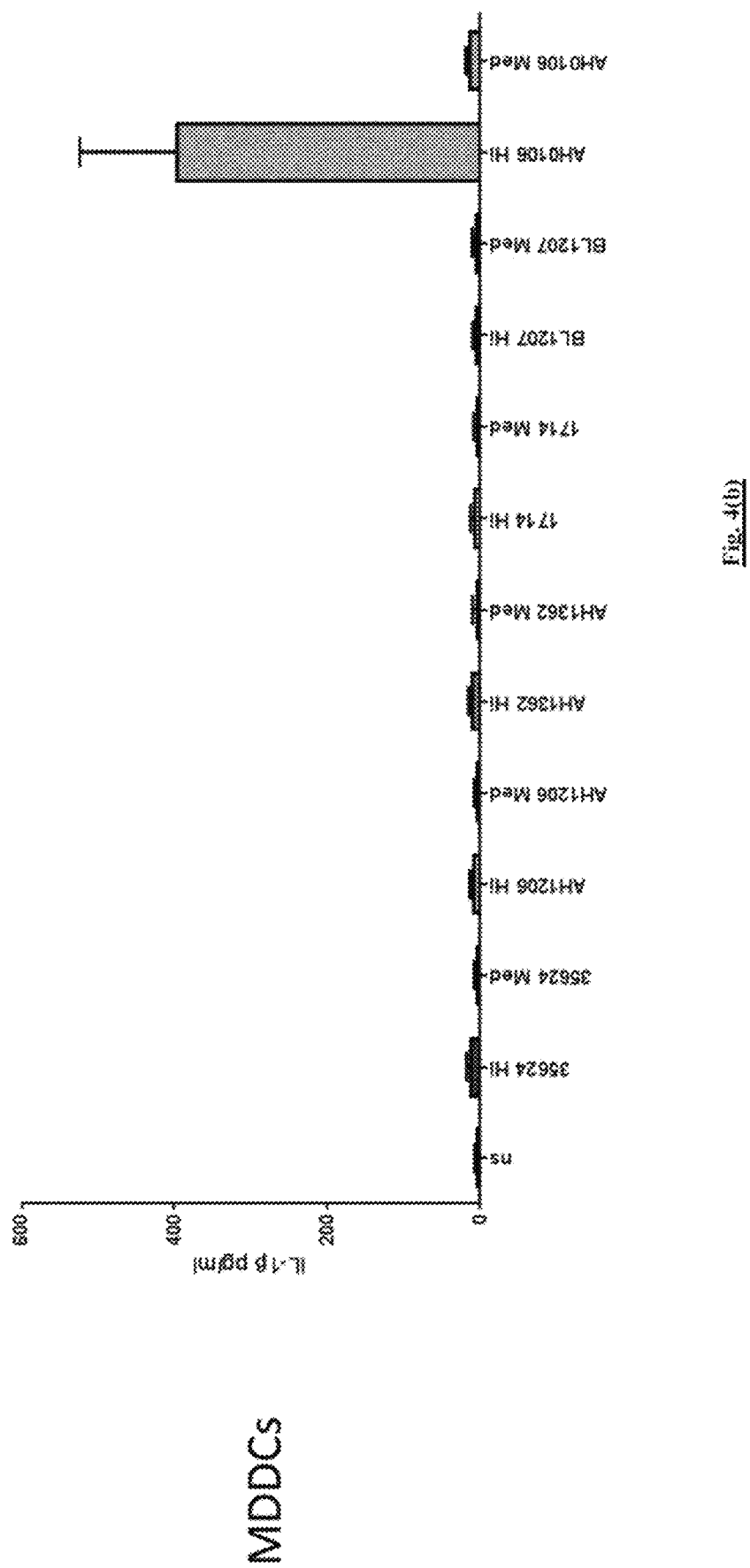

A deposit of *Bifidobacterium longum* strain AH0106 was made at the National Collections of Industrial and Marine Bacteria Limited (NCIMB) Ferguson Building, Craibstone Estate, Bucksburn, Aberdeen, AB21 9YA, Scotland, UK on 2 Aug. 2012 and accorded the accession number NCIMB 42020.

The specification also refers to *Bifidobacterium longum* NCIMB 41003 (35624® strain). This strain is described in WO00/42168, the entire contents of which are incorporated herein by reference. The strain was deposited at the National Collection of Industrial and Marine Bacteria, Ferguson Building, Craibstone Estate Bucksburn, Aberdeen, AB21 9YA, Scotland, United Kingdom on Jan. 13, 1999.

We have discovered that a particular bacterial strain promotes anti-viral defence and inhibits damaging pro-inflammatory responses and are particularly useful in the prevention and/or treatment of virus induced ARDS, or viral-induced exacerbations in asthma and COPD patients.

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example 1 Isolation of *Bifidobacterium longum* NCIMB 42020

*Bifidobacterium longum* strain NCIMB 42020 was isolated from faecal samples from healthy human subjects.

Faecal samples were screened for probiotic bacterial strains. Samples were transferred to a collection tube containing Phosphate Buffered Saline (PBS), supplemented with 0.05% cysteine-HCl). The solutions were then incubated for 10 min. The samples were vortexed and plated on selective agar (De Man, Rogosa and Sharpe (MRS) agar+ 10% sucrose+Mupirocin and Congo red+cysteine+Mupirocin). A Congo red agar screen was used to phenotypically screen for EPS expressing bacterial strains. Briefly, 10 ml Modified Rogosa broth media (+0.05% cysteine) was inoculated aseptically with a freshly grown colony of the bacterial strain and incubated anaerobically at 37° C. until turbid (about 16 to about 24 hours). The broth cultures were aseptically streaked onto Congo Red Agar plates and incubated anaerobically at 37° C. for 48 hours. It is believed that EPS produced as a by-product of the growth and/or metabolism of certain strains prevents the uptake of the Congo red stain resulting in a cream/white colony morphology. Stains that produce less EPS take up the Congo red stain easily, resulting in a pink/red colony morphology. Strains that do not produce an EPS stain red and look almost transparent in the red agar background.

Isolated colonies were picked from the plates and re-streaked three times to ensure purity. Microscope examination, Gram staining, Catalase testing, Fructose-6-Phosphate Phosphoketolase assessment were used to determine presumptive Bifidobacteria species and isolates were stocked in 40% glycerol and stored at −80° C. 16S intergenic spacer region sequencing (IGS) were used to confirm the identity of the newly isolated strains.

Following isolation of a pure bifidobacteria strain, assigned the designation AH0106, it was subsequently deposited at the NCIMB and given the designation 42020. Microbiological characteristics were assessed and are summarized in Table 1 below. *B. longum* NCIMB 42020 is a gram positive, catalase negative pleomorphic shaped bacterium which is Fructose-6-Phoshate Phosphoketolase positive, confirming its identity as a *bifidobacterium*.

TABLE 1

Physiochemical characteristics of *B. longum* NCIMB 42020

| Strain Characteristics | *B. longum* NCIMB 42020 |
| --- | --- |
| Gram Stain | + |
| Catalase | − |
| Motility | − |
| F6PPK* | + |

16s-23s intergenic spacer (IGS) sequencing was performed to identify the species of Bifidobacteria isolated. Briefly, DNA was isolated from NCIMB 42020 using 100 µl of extraction Solution and 25 µl of Tissue Preparation solution (Sigma, XNAT2 Kit). The samples were incubated for 2 hours at room temperature followed by 2 hrs at 95° C. and then 100 µl of Neutralization Solution (Sigma, XNAT2 kit) was added. Genomic DNA solution was quantified using a Nanodrop spectrophotometer and stored at 4° C. PCR was performed using the IGS primers. The primer pairs used were IGS R 5'-CTGGTGCCAAGGCATCCA-3' (SEQ ID No. 1) and IGS L 5'-GCTGGATCACCTCCTTTCT-3' (SEQ ID No. 2). The cycling conditions were 94° C. for 4 min (1 cycle), 94° C. for 45 sec, 53° C. for 45 sec, 72° C. for 45 sec (28 cycles). The PCR reaction contained 2l (100 ng) of DNA, PCR mix (Sigma, Red Taq), 0.025 nM IGS L and R primer (MWG Biotech, Germany). The PCR reactions were performed on a Biotherma thermocycler. The PCR products (10 µl) were ran alongside a molecular weight marker (100 bp Ladder, Roche) on a 2% agarose EtBr stained gel in TAE, to determine the IGS profile. PCR products of *Bifidobacterium* (single band) were purified using the Promega Wizard PCR purification kit. The purified PCR products were sequenced using the primer sequences (above) for the intergenic spacer region. Sequence data was then searched against the NCBI nucleotide database to determine the identity of the strain by nucleotide homology. The resultant DNA sequence data was subjected to the NCBI standard nucleotide-to-nucleotide homology BLAST search engine (http://www.ncbi.nlm.nih.gov/BLAST/). The nearest match to the sequence was identified and then the sequences were aligned for comparison using DNASTAR MegAlign software. The sequences can be viewed in the sequence listing (Table 2). Searching the NCIMB database revealed that NCIMB 42020 has a unique IGS (Table 2) sequence with its closest sequence homology to a *Bifidobacterium longum*.

TABLE 2

IGS sequence B. *longum* NCIMB 42020 (SEQ ID No. 3)
TTGCTGGGATCACCTCCTTTTTACGGAGAATTCAGTCGGATGTTCGTCCGA

CGGTGTGCGCCCCGCGCGTCGCATGGTGCGATGGCGGCGGGGTTGCTGGTG

TGGAAAACGTCGTTGGCTTTGCCCTGCCGGTCGTGCGGTGGGTGCGGGGTG

GTATGGATGCGCTTTTGGGCTCCCGGATCGCCACCCCAGGCTTTTTGCCTG

GCGCGATTCGATGCCCGTCGTGCCTGGGGGCCGGCCGTGTGCCGGCGCGAT

GGCGTGGCGGTGCGTGGTGGCTTGAGAACTGGATAGTGGACGCGAGCAAAA

CAAGGGTTTTTGAATCTTTGTTTTGCTGTTGATTTCGAATCGAACTCTATT

GTTCGTTTCGATCGTTTTGTGATCATTTTTAGTGTGATGATTTGTCGTCCT

GGGAATTTGCTAGAGGAATACTTGCGGGCCATGCACTTTCGTGGTGTGTGT

TGCTTGCAAGGGCGTATGGTGGAGGCCTTGGCACCAGAA

Example 2—Cytokine Profile of AH106 and Comparison to the Profile of Other *Bifidobacteria Longum* Strains with Potential Health Benefits Peripheral blood mononuclear cells (PBMCs) were isolated from healthy donors using density gradient centrifugation. PBMCs were washed and resuspended in Dulbecco's Modified Eagle Medium-Glutamax (DMEM) TM (Glutamax (Glutamine substitute)+pyruvate+4.5 g/l glucose (Gibco catalog 10569-010) 10% fetal bovine serum (Sigma catalog F4135), and 1% penicillin/streptomycin (Sigma catalog P0781). PBMCs were stimulated with different doses of *Bifidobacteria longum* ((Total bacteria:PBMC) high (100:1) and mid (50:1)) for 24 h in supplemented DMEM at 37° C., 5% CO2.

For monocyte-derived dendritic cells generation: Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (Life Technologies, 21875-091) with interleukin 4 1000 U/ml (Novartis) and granulocyte macrophage colony stimulating factor (PeproTech, 300-03) 1000 U/ml for 6 days in order to differentiate them into monocyte-derived dendritic cells (MDDCs). MDDCs were stimulated with different doses of *B. longum* ((Total bacteria:MDDC) high (100:1) and mid (50:1)) for 24 h in cRPMI at 37° C., 5% CO2. Cytokine secretion was measured using a commercial cytokine kits (MesoScale Discovery) platform following the manufacturers' instructions.

AH0106 induced more IL-10, IL-12p40, TNF-α, IL-11 in both PBMCs and MDDCs than all of the other bacterial strains (35624, AH1206, AH1362, 1714, BL1207) which gave similar profiles to each other (FIGS. 1 to 4). AH106 is a much more potent stimulator of cytokines than the other *B. longum* especially known anti-inflammatory strains such as 35624 and 1714 and demonstrates that AH0106 engages with the human immune system in a different way to the other *B. longum* strains in a manner which is more immune-stimulatory.

Example 3: AH0106 Strain (Beneficially Blocks Type 1 Interferons and Resultant IP-10 Induction (a Pro-Inflammatory Chemokine) and Increase Type 3 Interferon IFN-λ in Monocyte Derived Dendritic Cells)

Figure 5:
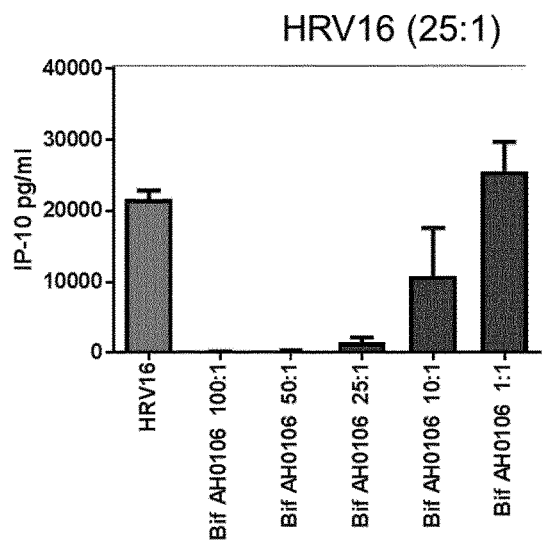
FIG. 5 is a bar chart of the IP-10 response to rhinovirus in the presence of *B. longum* AH0106.
Figure 6A:
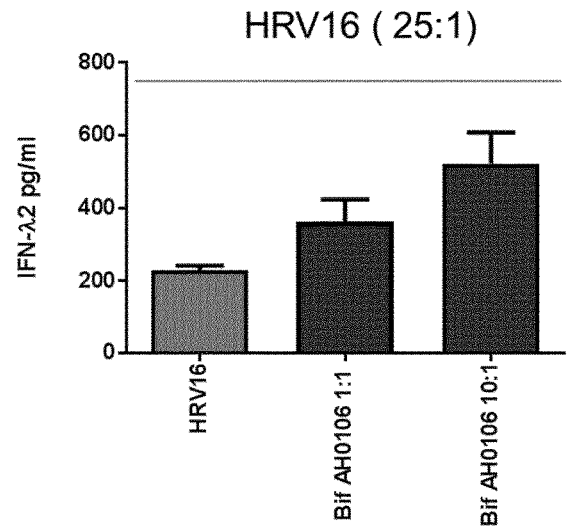
FIGS. 6(a) to 6(c) are a series of bar charts of interferon lambda (type III interferon), interferon alpha and interferon beta (type 1 interferon) responses to rhinovirus in the presence of *B. longum* AH0106.
Figure 6B:
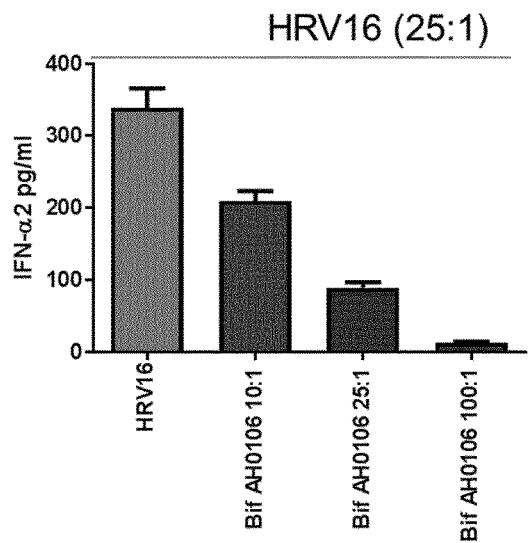
Figure 6C:
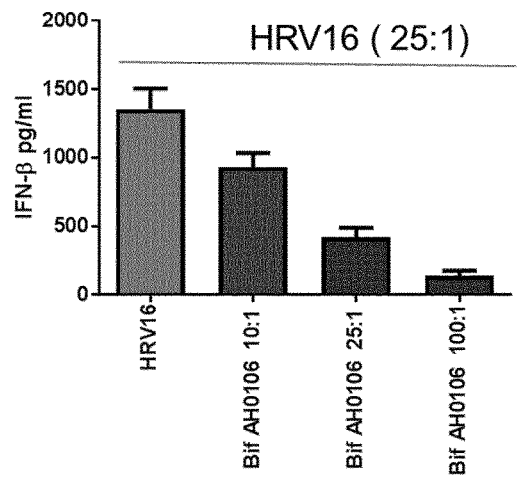

The excessive immune response by dendritic cells to viral infection causes pro-inflammatory responses in the lung. Type 1 IFNs can stimulate the production of IP-10 a chemokine which binds is a chemoattractant for Th1 cells. To determine if a *B. longum* AH0106 might have a beneficial anti-viral effect, on human monocyte-derived dendritic cells, MDDCs were stimulated with *B. longum* AH0106 before being exposed to Human rhinovirus 16 (HRV16) and the interferons and IP-10 response to HRV16 was monitored. MDDCs were stimulated with HRV16 (MOI) 25:1) for 24 h in cRPMI at 37° C., 5% CO2 following pre-treatment (1 h) with multiple doses of *B. longum* AH0106 (100:1, 50:1, 25:1, 10:1, 1:1) or just HRV16 alone. Cytokine secretion was examined by Bio-Plex multiplex suspension array (Bio-Rad Laboratories) measuring IFN-α, IFN-β, IFN-λ and IP-10. Surprisingly, the IP-10 response to RV was attenuated by *B. longum* AH0106 strain in a dose-dependent manner (FIG. 5). Equally surprising, was that co-incubation with *B. longum* AH0106 strain, at lower doses, resulted in the enhancement of type III interferon responses (Interferon lambda) while Interferon alpha and beta responses were suppressed at higher doses, similar to the IP-10 response (FIG. 6). The data shows that *B. longum* AH0106 alters the immune response to RV in supporting a protective immune response while dampening the damaging responses.

Example 4: Not all Gram Positive Bacterial Strains have the Same Effect

Figure 7:
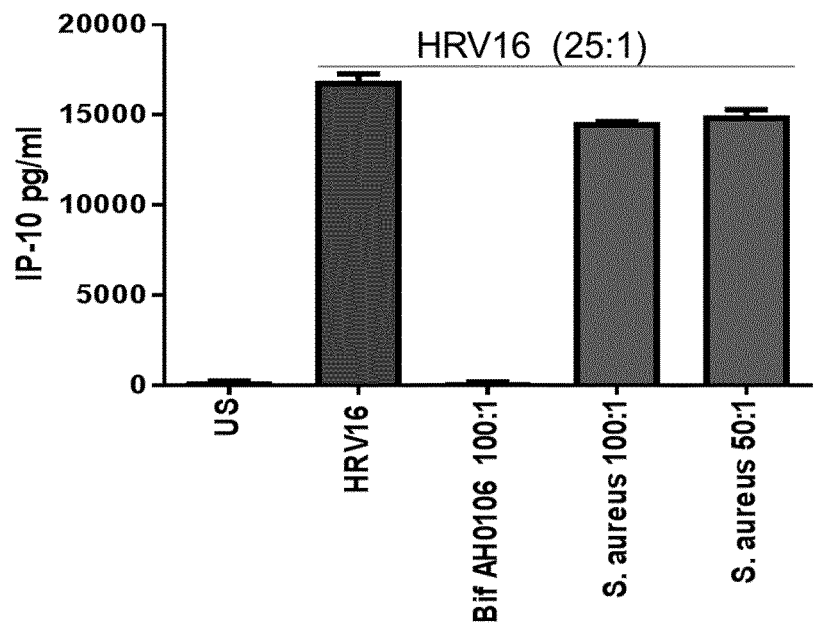
FIG. 7 is a bar chart comparing the IP-10 response to rhinovirus 16 in the presence of *B. longum* AH0106 or a *Staphylococcus aureus* strain.

To determine if another gram positive bacterial strain might have a beneficial anti-viral effect, on human monocyte-derived dendritic cells, MDDCs stimulated with *Staphylococcus aureus* were exposed to human rhinovirus 16 (HRV16) and the IP-10 response monitored. Briefly, MDDCs were stimulated with HRV16 (MOI) 25:1) for 24 h in cRPMI at 37° C., 5% CO2 following pre-treatment (1 h) with multiple doses of *Staphylococcus aureus* (100:1, 50:1) compared to *B. longum* AH0106 (100:1) or just HRV16 alone. The *Staphylococcus aureus* strain did not reduce DC IP-10 secretion in response to HRV16 (FIG. 7).

Figure 8:
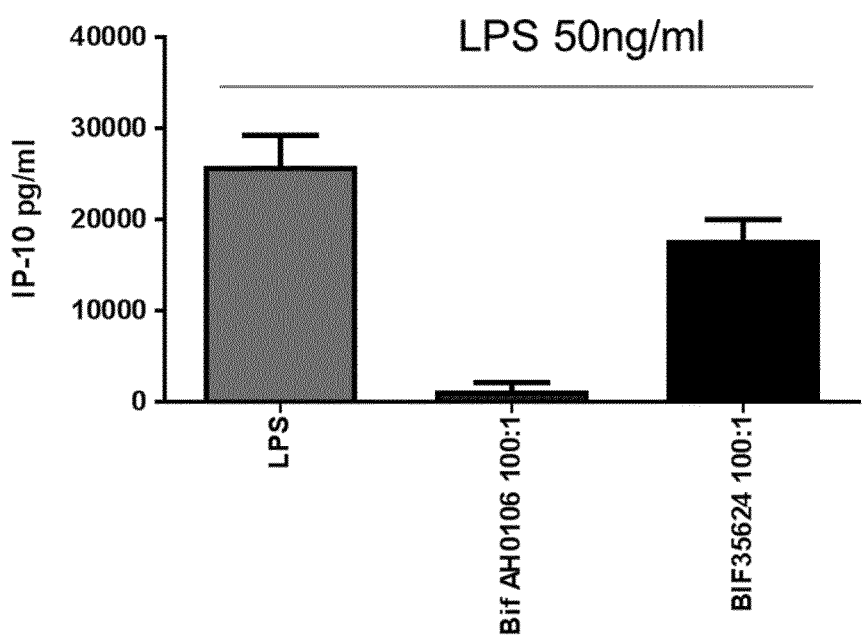
FIG. 8 is a bar chart of the IP-10 response to LPS in the presence of *B. longum* strains AH0106 and 35624.

Example 5: AH0106 Strain Beneficially Blocks TNF-α as Well as IP-10 in Monocyte Derived Dendritic Cells but not all *Bifidobacteria Longum* Strains have the Same Effect Within the inflamed mucosa, it is not just the virus itself that induces IP-10 and TNF-α secretion, but also other (toll like receptor) TLR ligands can induce its production. Therefore, MDDCs were pretreated with *B. longum* AH0106 or *B. longum* 35624 before being exposed to LPS. The IP-10 and TNF-response to LPS a TLR-4 agonist was monitored. Briefly, MDDCs were stimulated with LPS (50 ng/ml) for 24 h in cRPMI at 37° C., 5% CO2 following pre-treatment (1 h) with *B. longum* AH0106 or 35624 at a dose of (100:1) or just LPS alone. Surprisingly, the IP-10 and TNF-α response to LPS was attenuated by *B. longum* AH106 whereas there was only a slight reduction in IP-10 response to LPS after exposure to *B. longum* 35624 (FIG. 8) and *B. longum* 35624 increases TNF-α at the same dose (FIG. 9). This is a very surprising result as *B. longum* 35624 is a well-known anti-inflammatory strain and was the hypothesised top candidate. Some of the cytokine data on *B. longum* AH0106 suggested that it would cause a generalised immunestimulatory reaction but in practice *B. longum* AH0106 had a superior and specific immune response in this cell system.

Example 6—Comparison of *B. longum* AH106 and *B. longum* 35624 in a Pre-Clinical In Vivo Model of Respiratory Infection We tested the efficacy of *B. longum* AH0106 strain in pre-clinical models designed to show therapeutic benefit. Rhinovirus murine models are not considered to be good surrogates of human infection as mice do not have ICAM, the receptor for major group rhinoviruses to enter the cell. Therefore, we utilized a lethal influenza model in mice, which is considered a better model (Bartlett et al, 2015). The H1N1 influenza strain A/PR8/34 (100 PFU/50 ul) strain was used to infect mice.

Figure 20:
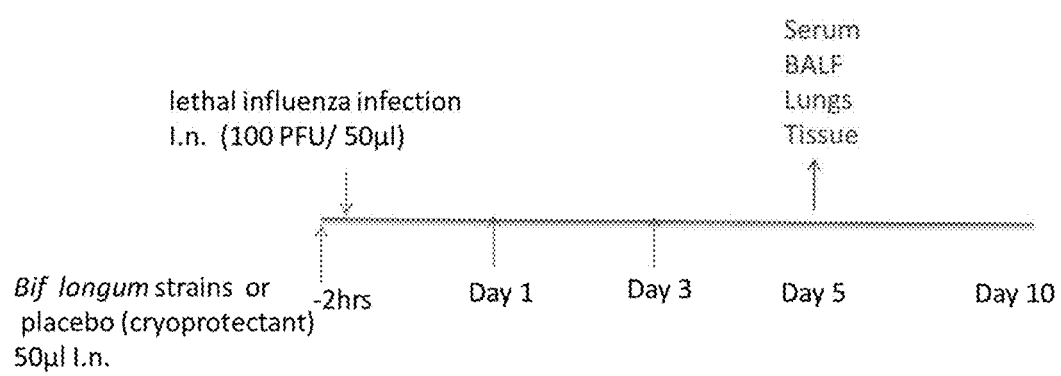
FIG. 20 is an administration schedule discussed in Example 6.

The *B. longum* AH0106 strain, *B. longum* 35624 strain or placebo was administered intranasally at −2 hours, +1 day, and +3 days following viral infection (FIG. 20). These strains were administered at a dose of $1 \times 10^9$ total cells.

2 h, day 1, and 3 administration of vehicle control (Group 1), *B. longum* AH0106 (Group 2 and *B. longum* 35624 cell wall fraction (Group 3) per nasal (in 50 μl volume).

Day 0 Administration of a dose of lethal influenza (PR8) per nasal (Group 1-3).

Day 0-10 Monitoring of animals for morbidity (weight, temperature and clinical score, Group 1-3).

Day 5: 5 animals per group are sacrificed for terminal bleed, organ removal and analysis on each day. Day 5 (Group 1-3).

Day 5: Isolation of BAL fluid for the measurement of cytokines and cell infiltrates. Collection of the lung tissue for the quantification of viral titre in the lung by quantitative PCR (half of all lung lobes).

Measurement of Viral Titre in Lung Tissue.

Lung lobes isolated were prepared for the quantification of viral load in lung tissue by quantitative PCR. RNA was prepared with TRI Reagent (Molecular Research Center) and then treated with DNase (Invitrogen) to avoid genomic DNA contamination before RNA was converted to cDNA by reverse transcription using SuperScript III (Invitrogen). cDNA was quantified by real-time PCR (iCycler; Bio-Rad) using SYBR Green (Stratagene) and samples were normalized with GAPDH expression levels. Primers sequences (forward and reverse, respectively) used were influenza PR8 M protein, 5'-GGACTGCAGCGTAGACGCTT-3' (SEQ ID No. 4) and 5'CATCCTGTATATGAGGCCCAT-3' (SEQ ID No. 5).

Groups (1-3):

1. Treatment with Placebo—cryoprotectant resuspended in PBS.

2. Treatment with *B. longum* AH0106 10^9 total cells.

3. Treatment with *B. longum* 35624 10^9 total cells

Number of mice per group (Group 1-3)=5

Measurements of Cytokines and Chemokine.

The concentrations of mouse IL-1β, IL-2, IL-4, IL-5, IL-6, IL-9, IL-10, IL-12p70, IL-12/IL-23p40, IL-13, IL-15, IL-16, IL-17A, IL-17A/F, IL-17C, IL-17E, IL-17F, IL-21, IL-22, IL-23, IL-30, IL-31, IL-33, IP-10, MIP3α, MIP-2, MIP-1β, MIP-1α, MCP-1, KC/GRO, TNF-α, VEGF, EPO, GM-CSF, IFN-γ in both serum and BAL fluid were measured using a commercial U-PLEX Biomarker Group 1 Mouse 35-Plex (MesoScale Discovery) platform following the manufacturers' instructions; mouse IL-28 (IFN-λ 2/3), mouse G-CSF, mouse TRAIL, mouse AREG were detected using ELISA kits (RayBiotech, Inc); Oncostatin M and mouse surfactant protein D (SPD) were measured using Quantikine kits from R&D Systems following the manufacturer's instructions. Mouse IFN-α was measured in serum and BAL fluid by mouse IFN alpha platinum ELISA (ThermoFisher scientific) Serum and BAL fluid levels of mouse interferon-β (IFN-β) were measured using VeriKine Mouse Interferon Beta HS ELISA Kits (PBL Assay Science).

Measurement of Cellular Infiltrates into BAL.

Cells were isolated from the BAL fluid and total cell numbers in the bronchoalveolar lavage (BAL) fluid was determined using a Coulter Counter (IG Instrumenten-Gesellschaft AG, Basel, Switzerland). Differential cell counts were performed (200 cell counts/samples) based upon standard morphological and cytochemical criteria on cytospins stained with Diff-Quik solution (Dade Behring, Siemens Healthcare Diagnostics, Deerfield, Ill.).

Figure 12:
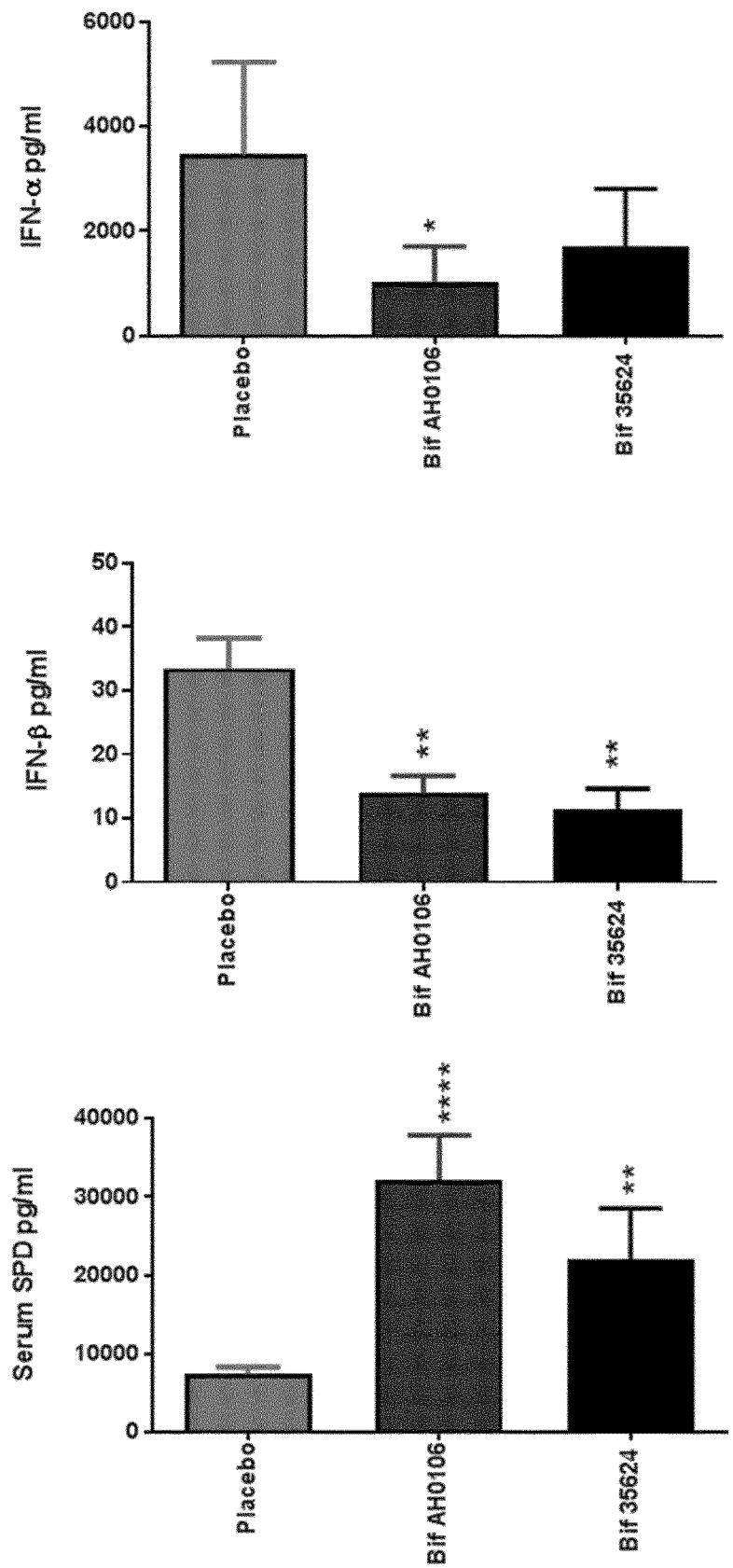
FIG. 12 is a series of graphs of cytokine responses in the Bronchoalveolar lavage (BAL) fluid and surfactant protein D responses in the serum to strains *B. longum* strains AH0106, 35624, and placebo following viral infection.
Figure 13:
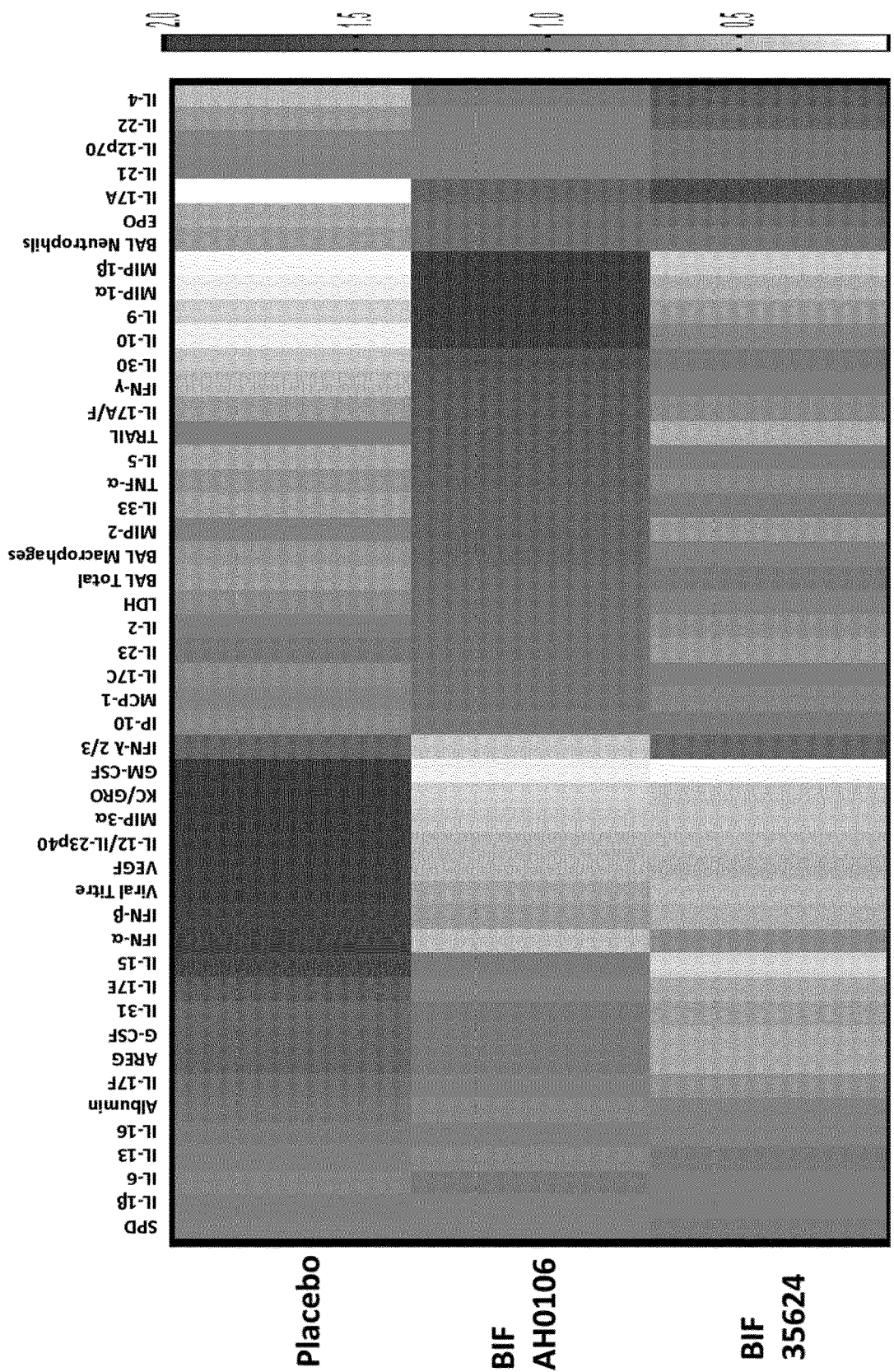
FIG. 13 shows a heat map of different biomarkers measured in the BAL in responses to strains *B. longum* strains AH0106, 35624 and placebo following viral infection; The higher the intensity of band the greater the induction.
Figure 14:
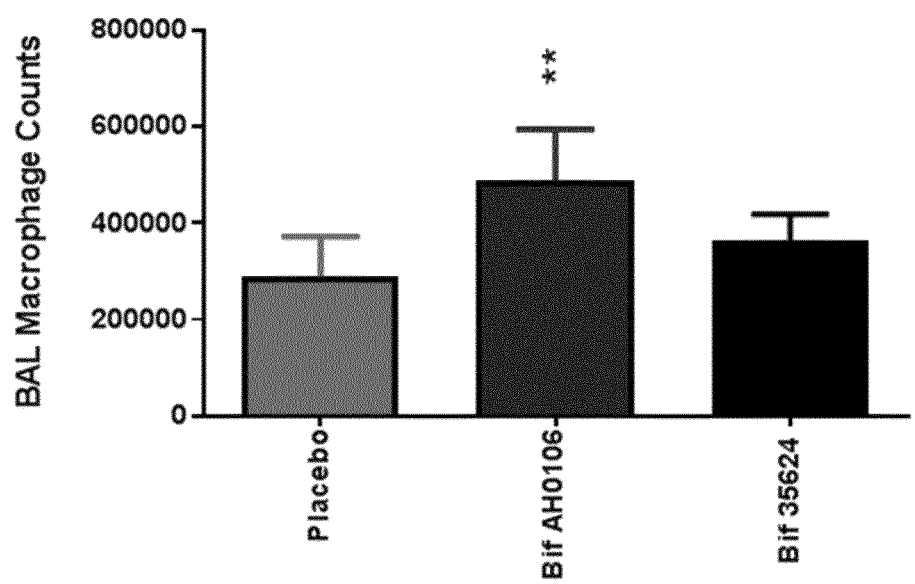
FIG. 14 is a graph of BAL count of Macrophages in response to the strains *B. longum* strains AH0106, 35624 and placebo, following viral infection.
Figure 15:
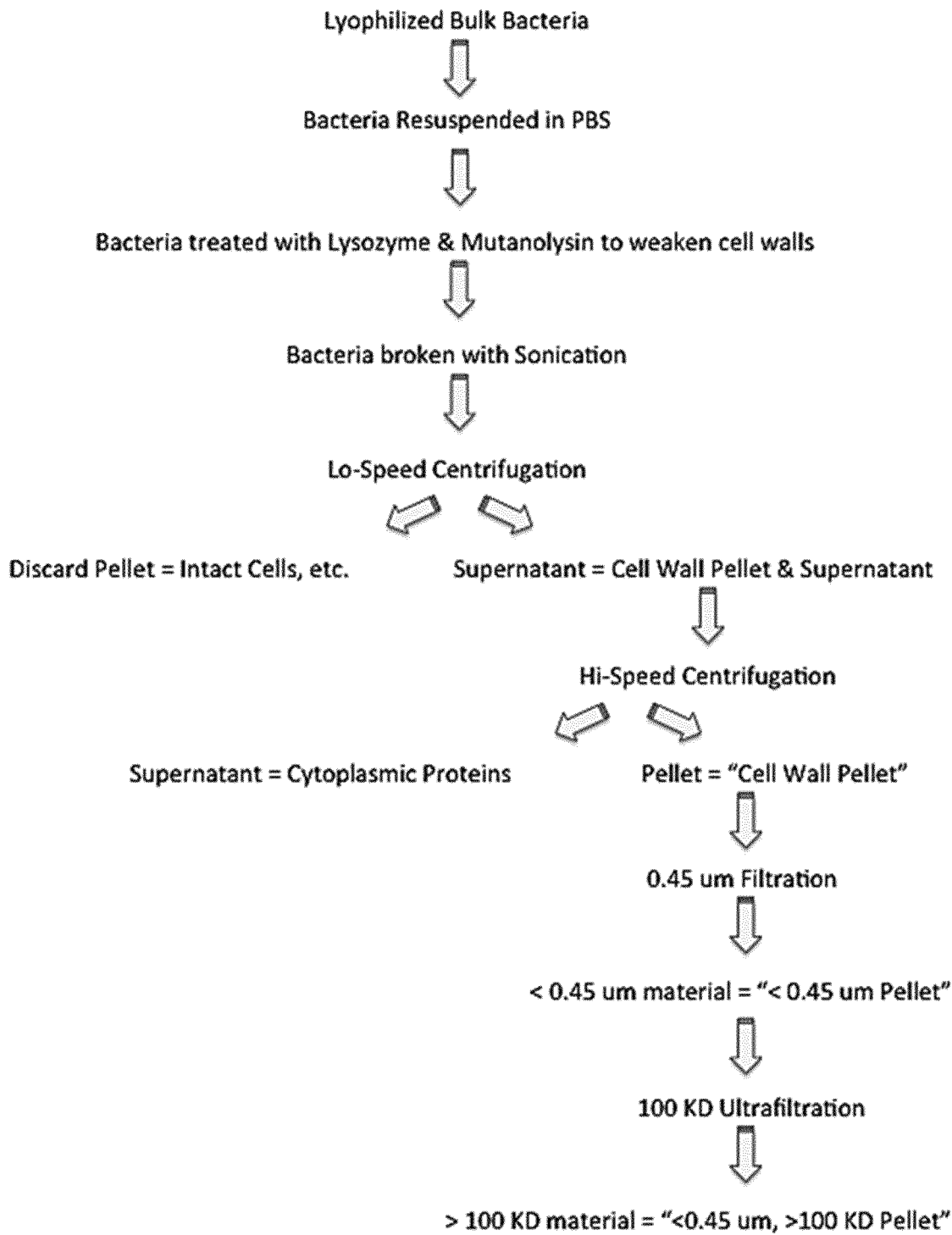
FIG. 15 is a flow chart of a process used for isolating a cell wall fraction from *Bifidobacterium longum* AH0106.

Surprisingly, administration of the *B. longum* AH0106 protected the mice better than the *B. longum* 35624 strain. Viral titre was reduced by similar levels in both strains (FIG. 10) but mortality was reduced more in the *B. longum* AH0106 treated mice (FIG. 11). This enhanced survival was associated with a reduced interferon-alpha and interferon-beta response and an enhanced surfactant protein D response (FIG. 12). In addition, there was a potent induction of cytokines and chemokines in AH0106 treated animals (FIG. 13) associated with the increase in macrophages in the BAL at day 5 (FIG. 14). This immune response contributed to the enhanced viral clearance seen in the *B. longum* AH0106 treated animals and the start of the healing process brought the influx of macrophages into the lung.

Example 7—Cell Wall Pellet Generation

Bacterial Harvesting/Washing
Method:
1. The equivalent of 250 ml of original bacterial biomass (total cell count=$1.5\times10^{11}$) is harvested by centrifugation (14000 rpm, 4° C., 20 min; rotor JA-20 (Avanti J-26× P Beckman Coulter). The bacterial pellet is washed with sterile PBS and the supernatant is discarded and washed again (repeat two more times).
2. For viable and non-viable lyophilised bacteria (0.5 g of $3.0\times10^{11}$ powder or total cell count=$1.5\times10^{11}$) was resuspended in 50 mls and harvested by centrifugation (14000 rpm, 4° C., 20 min; rotor JA-20 (Avanti J-26× P Beckman Coulter). The bacterial pellet is washed with sterile PBS and the supernatant is discarded and washed again (repeat two more times).
3. Finally the pellet is resuspended in 50 ml of sterile PBS and the bacterial solution divided into two 25 ml aliquots Cell Disruption The aim of this procedure was for the generation of a cell wall fraction from the whole bacteria and the elimination of the cytoplasmic fraction and other components. This involves one or more steps selected from:

treatment with a chelating agent optionally in conjunction with freeze thaw procedure to prevent DNAse or protease activity when using enzymatic treatment to aid lysis Enzymatic treatment with a glycoside hydrolase and/or N acetylmuramidase Application of shear force such as ultra-sonication or application of high pressure such as using a French press.

Separation of the cell wall fraction from the cytoplasmic fraction by using centrifugation Filtration of the cell wall fraction Materials:

EDTA (0.5M Fluka) is chelator for removal of metal ions (calcium or magnesium) to prevent DNAse or protease activity when using enzymes for cell wall lysis Lysozyme (Sigma 10 mg/ml) *endotoxin free is a glycoside hydrolase that catalyses the hydrolysis of 1,4-beta-linkages between N-acetylmuramic acid and N-acetyl-D-glucosamine residues. This hydrolysis compromises the integrity of bacterial cell walls causing lysis of the bacteria.

Mutanolysin (10 KU Sigma diluted in 1 ml $H_2O$) is an N-acetylmuramidase, which is an muralytic enzyme that cleaves the β-N-acetylmuramyl-(1→4)-N-acetyl-glucosamine linkage of the bacterial cell wall. This cleavage compromises the integrity of bacterial cell walls causing lysis of the bacteria.

Glass beads 90-150 μm particle size (VWR) used in conjunction with sonication to aid lysis Method:
1. Add 250p1 EDTA (0.5M stock Fluka) to each of the 25 ml aliquots therefore having a final concentration of 5 mM EDTA.
2. Freeze the aliquots by placing the 2 aliquots in liquid nitrogen till frozen then thaw the aliquots in water; repeat this procedure twice.
3. Each 25 ml of bacterial aliquot is incubated with 250 μl Lysozyme (10 mg/ml) and 250 μl Mutanolysin (2.5 KU) for 1 hour at 37° C. with an occasional mild vortex. From this step shear force is used either by a sonicator or a French press to disrupt the bacterial cell.

Sonication

A half teaspoon of autoclaved glass beads 90-150 μm particle size (VMR) were added to the bacterial aliquots just before sonication.

Sonicate 25 ml of resuspended bacterial material at a time, then put on ice and sonicate the other aliquot using the Sonicator (VibraCell SONICS) with the 50 ml probe. (Settings Tune=50, Frequency=60). This procedure is repeated four times for 10 minutes on ice. Following sonication, the glass beads, unbroken cells and cell debris are removed by centrifugation at 1000 rpm for 10 minutes at 4° C.

High Pressure with French Press

Alternatively, the bacterial cells are disrupted by pressure of 1500 psi on the high setting (20,000 psi equivalent) using a French press (Thermo Electron Corporation FA-078A). This procedure is repeated three times on ice.

Application of a shear force using the French press results in a clearing of the turbid bacterial cells after the third run. Following French press disruption, the unbroken cells and cell debris are removed by centrifugation at 1000 rpm for 10 minutes at 4° C. and the supernatant containing the cell wall material and cytoplasmic fractions is retained.

4. Following application of a shear force (sonication or high pressure) a supernatant containing the cell wall material and cytoplasmic fractions was retained. This supernatant is centrifuged for 20 min at 14000 rpm at 4° C. to separate the cell wall material from the cytoplasmic material. The supernatant is discarded.
5. The pellet containing the cell wall material is re-suspended in 5 ml of PBS per 250 ml of original bacterial biomass. The pellet of cell wall material was centrifuged at 1000 rpm for 10 minutes to remove black residue in the pellet. The pellet containing the cell wall material was stored at −80° C.

Centrifuges and Rotors
Avanti J-E Centrifuge Beckman Coulter
Rotors: JA-20
Sonicator
VibraCell SONICS, Sonics and Materials
Probe 435-09
French Press
French Press FA-078A
Cell FA-032 (40K Standard) (Standard FRENCH Pressure 40,000 psi Cell with 35 ml capacity, pressure up to 40,000 psi)
Size Filtration Followed by Ultrafiltration
Materials:
Polyvinylidene difluoride (PVDF) membrane filters (0.45 μm pore size, Millipore, Bedford, Mass.)
100 kDa MWCO UF device (Millipore).
1. The resuspended bacterial Pellet containing cell wall material (5 ml) is thawed and filtered through polyvinylidene difluoride (PVDF) membrane filters (0.45 μm pore size, Millipore, Bedford, Mass.; rinsed thoroughly with PBS before use). The material that comes through the membrane filter is free of intact bacteria and is a cell wall material having a size of <0.45 μm. 4 ml of cell wall material is produced by this 0.45 μm filter step. From the original 250 mls of bacterial culture, 4 ml of the suspended cell wall material remains.
2. The <0.45 μm cell wall material is then ultrafiltered.
   a. Rinse UF device first with 15 ml PBS, spin at 3500× g at 4° C.

b. Take the <0.45 μm bacterial Pellet extracts, load ~4 ml into the 100 kDa MWCO UF device.
c. When the >100 kDa upper solution gets lower in volume, diafilter with PBS.
d. The material that comes thru the 100 kDa filter will be retained and stored at −80° C.
e. The retentate should be resuspended in the same volume of PBS as was added to the ultrafiltration device (4 ml). This material is termed the >100 kDa bacterial Pellet. The final dry weight of the cell wall fraction thus produced is 120 mg in 4 mls of retentate which equates to a final concentration is 30 mg of cell wall fraction per 1 ml.
f. This cell wall fraction was concentrated for in vitro and in vivo tests for more enhanced solubility. To make more concentrated material than 30 mg/ml such as 300 mg/ml (10λ) or 150 mg/ml (5λ)>100 kDa bacterial Pellet solutions the cell wall fraction is just resuspended in 10 times or 5 times less volume than the starting material.

Example 8: The Cell Wall Fraction from the AH0106 (Beneficially Blocks Type 1 Interferons and Resultant IP-10 Induction (a Pro-Inflammatory Chemokine) in MDDCS To determine if a cell wall fraction from *B. longum* AH0106, as produced in example 7, might have a beneficial anti-viral effect the fraction was incubated on human MDDC's exposed to HRV16 and type 1 interferon and the cell IP-10 response was monitored. For monocyte-derived dendritic cells generation: Peripheral blood mononuclear cells (PBMCs) were isolated from healthy donors using density gradient centrifugation. Human peripheral blood monocytes were isolated using CD14 positive isolation with the MACS system (Miltenyi Biotec, 130-050-201). Cells were cultured in cRPMI media (Life Technologies, 21875-091) with interleukin 4 1000 U/ml (Novartis) and granulocyte macrophage colony stimulating factor (PeproTech, 300-03) 1000 U/ml for 6 days to differentiate them into MDDCs. Cells were cultured in cRPMI media (RPMI (Life Technologies, 21875-091)+10% fetal bovine serum (Sigma catalog F4135) and 1% penicillin/streptomycin (Sigma catalog P0781).

MDDCs were stimulated with HRV16 (MOI) 25:1) for 24 h in cRPMI at 37° C., 5% $CO_2$ following pre-treatment (1 h) with a cell wall fraction from *B. longum* AH0106 (30 mg/ml) or just HRV16 alone. Cytokine secretion was examined by Bio-Plex multiplex suspension array (Bio-Rad Laboratories) (IFN-α, IFN-β, IP-10).

Figure 16A:
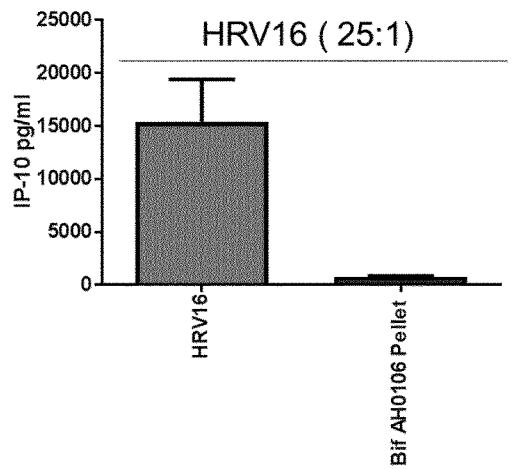
FIG. 16(a) is a graph of the IP-10 response to human rhinovirus (HRV16) in the presence of a cell wall fraction (Bif AH0106 pellet) from strain AH0106 in Monocyte Derived Dendritic cells.
Figure 16B:
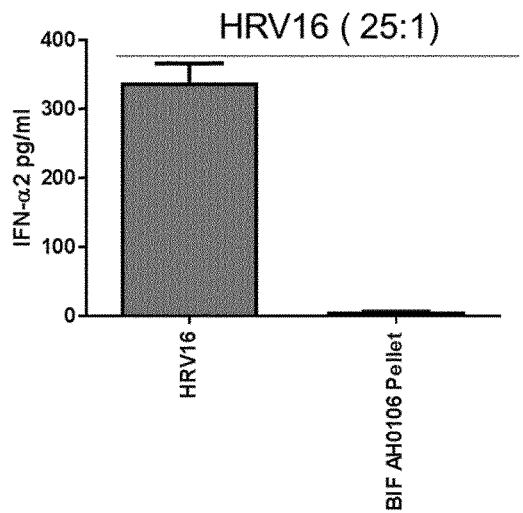
FIG. 16(b) is a graph of the IFN-α response to human rhinovirus (HRV16) in the presence of a cell wall fraction (Bif AH0106 pellet) from strain AH0106 in Monocyte Derived Dendritic cells.
Figure 16C:
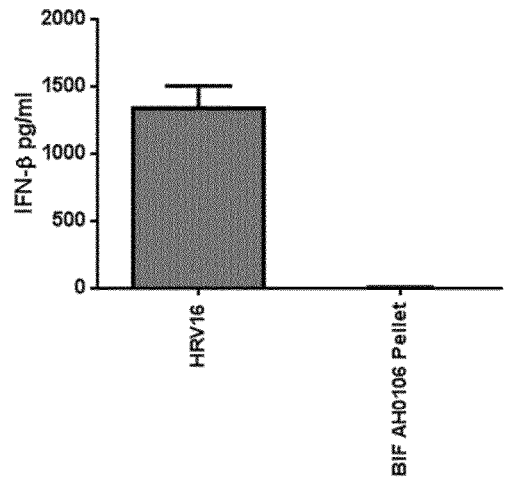
FIG. 16(c) is a graph of the IFN-β response to human rhinovirus (HRV16) in the presence of a cell wall fraction (Bif AH0106 pellet) from strain AH0106 in Monocyte Derived Dendritic cells.

In agreement with the HRV16 stimulated MDDC pre-treated with the *B. longum* AH0106 strain results above, the IP-10 (FIG. 16(a)), IFN-α (FIG. 16(b)), and IFN-β (FIG. 16(c)) response to HRV16 was attenuated by a cell wall fraction from the *B. longum* AH0106 strain.

Figure 17A:
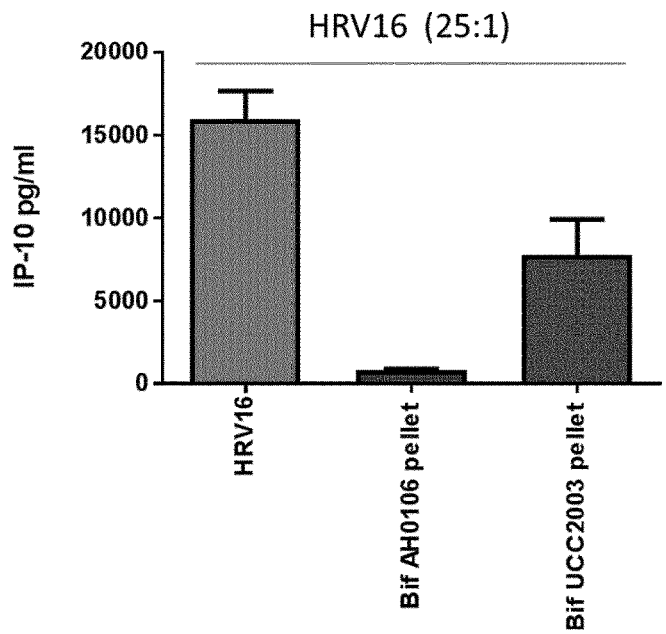
FIG. 17(a) is a bar chart of the IP-10 response to human rhinovirus (HRV16) in the presence of a cell wall fraction from strain UCC2003 compared to a cell wall fraction from strain AH0106 in Monocyte Derived Dendritic cells.

Example 9: Not all Cell Wall Fractions from Bifidobacteria Species have the Same Effect Cell wall fraction from another Bifidobacteria, *Bifidobacteria breve* (Bif UCC2003) was also tested using the methodology described in example 4 and did not show similar significant effects. The Bif UCC2003 fraction reduced IP-10 production following viral stimulation but not to the same extent as the *B. longum* AH0106 cell wall fraction during a 24 hours assay (FIG. 17(a)).

Figure 17B:
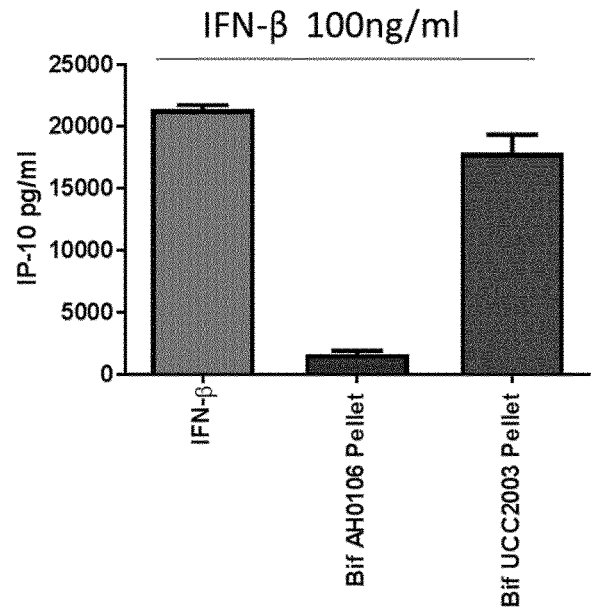
FIG. 17(b) is a bar chart of the IP-10 response to interferon beta (IFN-β) in the presence of a cell wall fraction from strain UCC2003 compared to a cell wall fraction from strain AH0106 in Monocyte Derived Dendritic cells.

Additionally, within the inflamed mucosa, it is not just the virus itself that induces IP-10 secretion; other cytokines can also induce IP-10 production. Cytokines such as IFN-β are produced as part of the primary anti-viral host response. IFN-β in particular is a potent inducer of IP-10. Therefore, we examined the effect of the cell wall fraction on secretion of IP-10 in response to IFN-β (FIG. 17(b)). MDDCs were stimulated with IFN-β (200 ng/ml) for 24 h in cRPMI at 37° C., 5% $CO_2$ following pre-treatment (1 h) with cell wall fractions (30 mg/ml) or IFN-β alone. The *B. longum* AH0106 cell wall pellet fraction suppressed IP-10 secretion to these stimuli, while the Bif UCC2003 cell wall pellet fraction did not reduce IP-10 secretion at all.

Figure 18A:
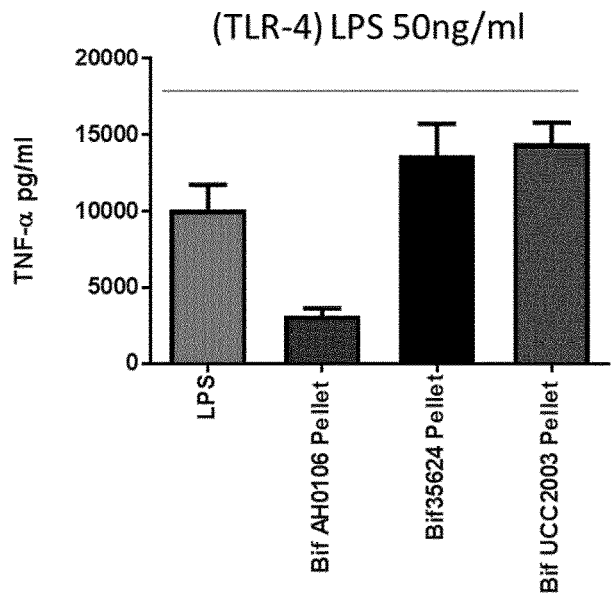
FIG. 18(a) is a bar chart of the TNF-α response to LPS in the presence of a cell wall fraction from strain UCC2003 compared to a cell wall fraction from *B. longum* strains AH0106 and 35624 in Monocyte Derived Dendritic cells.
Figure 18B:
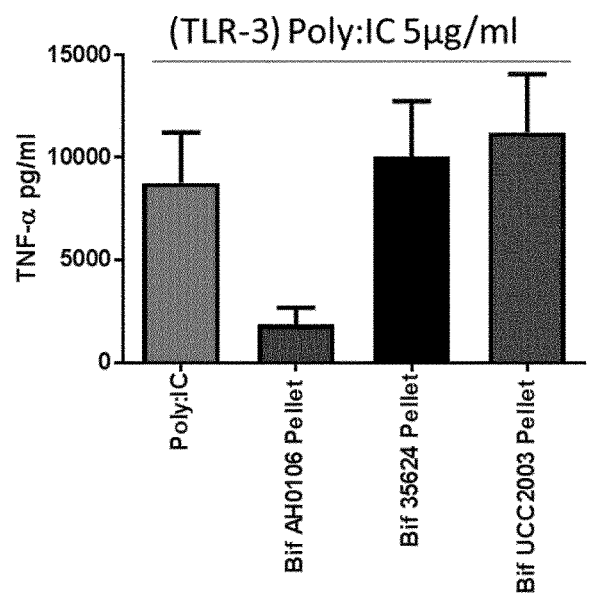
FIG. 18(b) is a bar chart of the TNF-α response to Poly:IC in the presence of a cell wall fraction from strain UCC2003 compared to a cell wall fraction from *B. longum* strains AH0106 and 35624 in Monocyte Derived Dendritic cells.

Example 10: The Cell Wall Fraction from *B. longum* AH0106 Strain has an Additional Beneficial Effect (Blocks TNF-α) in Monocyte Derived Dendritic Cells which Contribute to the Reduction of Inflammation and not all Bifidobacteria Strains have the Same Effect Within the inflamed mucosa, it is not just the virus itself that induces pro-inflammatory TNF-α secretion, but also other (toll like receptor) TLR ligands can induce its production. Therefore we examined the secretion of TNF-α in response to the TLR ligands Poly:IC (TLR-3) and LPS (TLR-4). MDDCs were pretreated with cells wall *B. longum* AH0106, *B. longum* 35624 and Bif UCC2003 before being exposed to LPS, a TLR-4 agonist, and the IP-10 and TNF-response to was monitored. MDDCs were stimulated with either the TLR-4 agonist LPS (50 ng/ml) or the TLR-3 agonist Poly:IC (5 μg/ml) for 24 h in cRPMI at 37° C., 5% $CO_2$ following pre-treatment (1 h) with cell wall fractions from Bifidobacteria at a dose of (30 mg/ml) or just the TLR agonist alone. TNF-α secretion was examined by Quantikine ELISA (R &D systems). In agreement with the results from the whole *B. longum* AH0106 strain the TNF-α response to LPS and Poly:IC was attenuated by the cell wall fraction from *B. longum* AH106 whereas both the cell wall fractions from *B. longum* 35624 and Bif UCC2003 increases TNF-α at the same dose (FIGS. 18a and 18b). This is a very surprising result as *B. longum* 35624 is a well-known anti-inflammatory strain and *B. longum* AH0106 had a superior response in this system.

Discussion

In summary, as illustrated in examples 2-10, we have shown there is an enhanced Type III interferon response which is beneficial, and addition of the cell wall fraction from AH0106 causes this desired response. In cells that are part of the later host immune system response (DC's) the cell wall fraction blocks the excessive Type 1 interferon response that can lead to cell damage and secondary infection. This targeted effect has benefit in infections caused by influenza, the common cold (rhino virus) and RSV, viral exacerbation of chronic respiratory diseases such as asthma, COPD and ARDs in both children and adults and in obese individuals.

Cascade Response

Figure 19A:
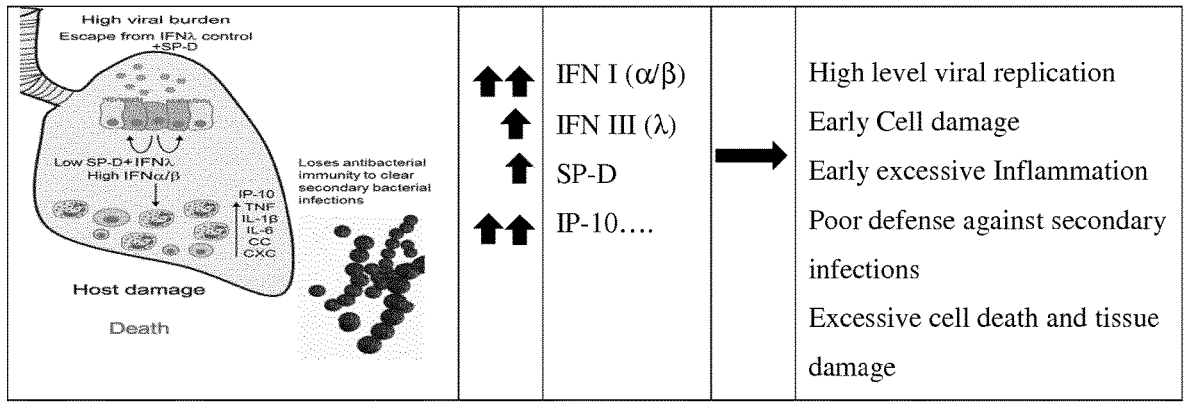
FIG. 19(a) is an illustration of cascade of abnormal response to a viral infection.

The cascade of abnormal response to viral infection is illustrated in FIG. 19(a).

Figure 19B:
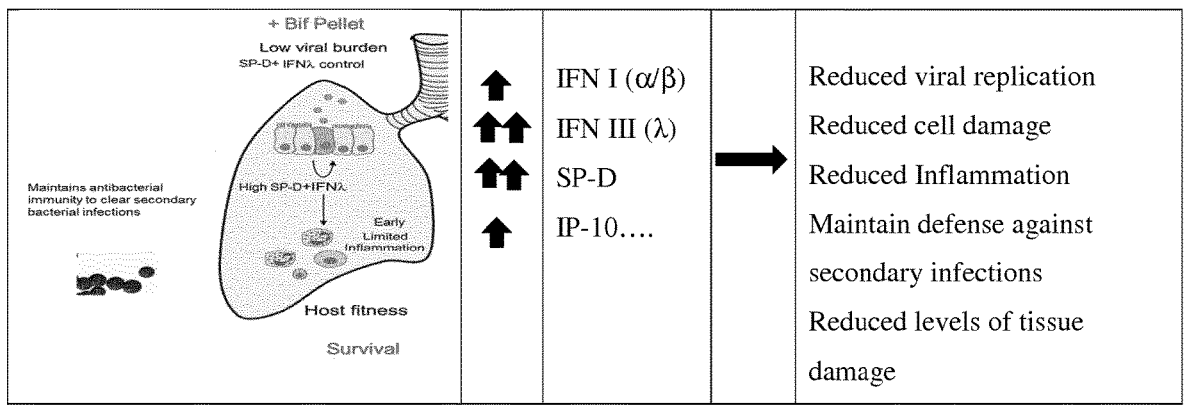
FIG. 19(b) is an illustration of cascade of response to a viral infection mediated by the strain or the cell wall fraction of *B. longum* AH106.

The cascade of AH0106 cell wall fraction mediated response to viral infection is illustrated in FIG. 19(b).

The main antiviral response is controlled by IFNs. The most well-defined type I IFNs are IFN-α and IFN-β. Most cell types produce IFN-β, whereas haematopoietic cells, particularly plasmacytoid dendritic cells, are the predominant producers of IFN-α (Ivashkiv and Donlin 2014). As mentioned previously, the Interferon type I responses, such as IFN-α and IFN-β has been shown to directly correlate with increased morbidity and mortality in models of influenza infection (Davidson et al, 2014). Type 1 IFNs can stimulate the production of IP-10 (also called CXCL-10) a chemokine which binds to CXCR3 where its primary function is a chemoattractant for Th1 cells. Lambda IFNs (IFN1s, type III IFNs or IL-28 and IL-29) constitute a newer class of interferons that share homology, expression patterns, and antiviral functions with type I IFNs (Lazear et al., 2015b; Wack et al., 2015). They induce downstream signalling that appears remarkably similar to that of type I IFNs, driving the expression of ISGs and the induction of antiviral responses (Durbin et al, 2013; Mendoza et al, 2017). However, type III interferons play an important role in limiting pro-inflammatory responses or immunopathology.

IP-10 is elevated in the lungs on infection with influenzas virus (Ichikawa et al, 2013). Indeed, blocking IP-10 using monoclonal antibodies ameliorates virus induced lung injury (Wang et al, 2013). IP-10 is elevated in the lungs of ARDS patients and it has been shown to be an important factor in the ARDS pathology (Ichikawa et al, 2013).

SP-D has an important role in innate host defence against influenza by binding to mannose-rich glycans on the HA/NA glycoproteins of the virus (Hartshorn et al, 1997; Reading et al, 1997; Hartshorn et al, 2000). SP-D mediates a range of antiviral activities in vitro, including neutralization of virus infectivity and inhibition of the enzymatic activity of the viral NA, and SP-D-deficient mice were more susceptible to infection with highly glycosylated influenza viruses. (Hartshorn et al, 1997; Reading et al, 1997; Tecle et al, 2007; LeVine et al, 2001; Vigerust et al, 2007; Hawgood et al, 2004). SP-D enhances phagocytosis and pulmonary clearance of RSV (LeVine et al, 2004).

Secondary bacterial infections are a major issue following viral infection. Virus-bacterial coinfection is well recognized with influenza, rhinovirus and RSV. The major bacterial infections in the respiratory tract include *Streptococcus pneumoniae, Moraxella catarrhalis*, and *Haemophilus influenzae* but *Staphylococcus aureus* has been also shown to cause serious infections post viral infection (Hewitt et al, 2016). Secondary bacterial infections occur most frequently at 5-10 days after primary viral infections, thus suggesting that a transient immunosuppression (the primary response) maybe responsible for the bacterial outgrowth. A mechanism proposed for a synergism between influenza and *S. pneumoniae* suggests that the antiviral type 1 IFN (IFN-α/β) response elicited by the primary influenza virus infection enhances the susceptibility of the host to secondary bacterial challenge via suppression of antibacterial immunity (Nakamura et al, 2011; Shahangian et al, 2009; Li et al, 2012). In contrast type III interferons such as IFN-λ can limit viral replication without inhibiting the clearance of the secondary bacterial infections which happens after IFN-α/β induction. It has been shown that the impact of attenuating IFN-λ signalling directly before bacterial challenge with an IFNLR1 Fc protein significantly increased bacterial burden in the lung compared with controls in animals (Rich et al, 2017). Furthermore, deficiency of SP-D was associated with enhanced colonisation and infection with *S. pneumoniae* of the upper and lower respiratory tract and earlier onset and longer persistence of bacteraemia. SP-D was shown to binds and agglutinates *Streptococcus pneumoniae* in vitro (a secondary bacterial infection agent that is a key problem in secondary exacerbations in asthma and COPD patients) (Jounblat et al, 2005).

The different conditions that are acutely affected by the dysregulated or aberrant immune response to viral infection are summarized as follows; Acute respiratory distress syndrome (ARDS), Asthma including childhood asthma, COPD, Obesity.

Acute respiratory distress syndrome (ARDS) affects a large number of people worldwide and is associated with a very high mortality rate (30-50%). Respiratory viral infections (e.g. influenza) are associated with ARDS.

Asthma is a chronic inflammatory disorder of the airways, usually associated with airway hyper-responsiveness and variable airflow.

Asthma is a chronic inflammatory disorder of the airways, usually associated with airway hyper-responsiveness and variable airflow obstruction that is often reversible spontaneously or during treatment (WHO, 2007). Approximately 80 to 85% of asthma exacerbations in children, adolescents, and less frequently adults are associated with viral upper respiratory tract viral infections, and rhinovirus (RV) accounts for ~60-70% of these virus-associated exacerbations. Viral infections are closely linked to wheezing illnesses in children of all ages. RSV is the main causative agent of bronchiolitis or croup, whereas rhinovirus (RV) is most commonly detected in wheezing children thereafter. Severe respiratory illness induced by either of these viruses is associated with subsequent development of asthma, and the risk is greatest for young children who wheeze with RV infections (Jartti and Gem, 2017).

Obesity is associated with dysregulated immune and inflammatory responses. The effect of obesity on the occurrence of asthma seems to be more prominent in women and non-allergic individuals, while there is a dose response effect of increasing body mass index (BMI) on asthma incidence. It is becoming increasingly evident that obesity is associated with a unique asthma phenotype that is characterized by more severe disease with variable response to conventional asthma therapies. In addition, obesity was identified as a risk factor for severe influenza during the 2009 influenza A (H1N1) pandemic and obese individuals have an impaired antiviral defence against respiratory viruses (Almond et al, 2013). Evidence suggests that it is not the virus itself but the nature of the immune response to RV that drives this damaging response (Steinke et al, 2016).

COPD is the third leading cause of death in the USA. In fact, COPD is the only major cause of death whose incidence is on the increase and is expected to be the third leading cause of death in the developed world by 2030 (exceeded only by heart disease and stroke). It results from inflammation induced damage of the airways causing chronic bronchitis and/or emphysema. A wider spectrum of viruses can induce exacerbations in COPD patients, but again it seems that it is not the virus, but the immune response to the virus that results in worsening of symptoms (Zhou et al, 2015).

It will be appreciated that the strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a bacterial component, a drug entity or a biological compound.

In addition a vaccine comprising the strains of the invention may be prepared using any suitable known method and may include a pharmaceutically acceptable carrier or adjuvant.

The human immune system plays a significant role in the aetiology and pathology of a vast range of human diseases. Hyper and hypo-immune responsiveness results in, or is a component of, the majority of disease states. One family of biological entities, termed cytokines, are particularly important to the control of immune processes. Perturbances of these delicate cytokine networks are being increasingly associated with many diseases. These diseases include but are not limited to inflammatory disorders, immunodeficiency, inflammatory bowel disease, irritable bowel syndrome, cancer (particularly those of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplantation, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis and acne vulgaris. The effects on cytokine production are specific for the probiotic strain-examined. Thus specific probiotic strains may be selected for normalising an exclusive cytokine imbalance particular for a specific disease type. Customisation of disease specific therapies can be accomplished using either a single strain of AN1206 or mutants or variants thereof or a selection of these strains.

The enteric flora is important to the development and proper function of the intestinal immune system. In the absence of an enteric flora, the intestinal immune system is underdeveloped, as demonstrated in germ free animal models, and certain functional parameters are diminished, such as macrophage phagocytic ability and immunoglobulin production. The importance of the gut flora in stimulating non-damaging immune responses is becoming more evident. The increase in incidence and severity of allergies in the western world has been linked with an increase in hygiene and sanitation, concomitant with a decrease in the number and range of infectious challenges encountered by the host. This lack of immune stimulation may allow the host to react to non-pathogenic, but antigenic, agents resulting in allergy or autoimmunity. Deliberate consumption of a series of non-pathogenic immunomodulatory bacteria would provide the host with the necessary and appropriate educational stimuli for proper development and control of immune function.

Inflammation is the term used to describe the local accumulation of fluid, plasma proteins and white blood cells at a site that has sustained physical damage, infection or where there is an ongoing immune response. Control of the inflammatory response is exerted on a number of levels. The controlling factors include cytokines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotropic and express multiple biologically overlapping activities. Cytokine cascades and networks control the inflammatory response rather than the action of a particular cytokine on a particular cell type. Waning of the inflammatory response results in lower concentrations of the appropriate activating signals and other inflammatory mediators leading to the cessation of the inflammatory response. TNFα is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. Such therapies may also play a significant role in the treatment of systemic inflammatory diseases such as rheumatoid arthritis.

The strain of the present invention may have potential application in the treatment of a range of inflammatory diseases, particularly if used in combination with other anti-inflammatory therapies, such as non-steroid anti-inflammatory drugs (NSAIDs) or Infliximab.

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour-bearing host. Complex cytokine interactions are involved in the regulation of cytokine production and cell proliferation within tumour and normal tissues. It has long been recognized that weight loss (cachexia) is the single most common cause of death in patients with cancer and initial malnutrition indicates a poor prognosis. For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory properties of *Bifidobacterium longum* these bacterial strains they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents. In general, species of *Bifidobacterium* have low activities of xenobiotic metabolizing enzymes compared to other populations within the gut such as *bacteroides*, eubacteria and clostridia. Therefore, increasing the number of *Bifidobacterium* bacteria in the gut could beneficially modify the levels of these enzymes.

The majority of pathogenic organisms gain entry via mucosal surfaces. Efficient vaccination of these sites protects against invasion by a particular infectious agent. Oral vaccination strategies have concentrated, to date, on the use of attenuated live pathogenic organisms or purified encapsulated antigens. Probiotic bacteria, engineered to produce antigens from an infectious agent, in vivo, may provide an attractive alternative as these bacteria are considered to be safe for human consumption (GRAS status).

Murine studies have demonstrated that consumption of probiotic bacteria expressing foreign antigens can elicit protective immune responses. The gene encoding tetanus toxin fragment C (TTFC) was expressed in *Lactococcus lactis* and mice were immunized via the oral route. This system was able to induce antibody titers significantly high enough to protect the mice from lethal toxin challenge. In addition to antigen presentation, live bacterial vectors can produce bioactive compounds, such as immunostimulatory cytokines, in vivo. *L. lactis* secreting bioactive human IL-2 or IL-6 and TTFC induced 10-15 fold higher serum IgG titres in mice immunized intranasally. However, with this particular bacterial strain, the total IgA level was not increased by co-expression with these cytokines. Other bacterial strains, such as *Streptococcus gordonii*, are also being examined for their usefulness as mucosal vaccines. Recombinant *S. gordonii* colonizing the murine oral and vaginal cavities induced both mucosal and systemic antibody responses to antigens expressed by this bacterial. Thus, oral immunization using probiotic bacteria as vectors would not only protect the host from infection, but may replace the immunological stimuli that the pathogen would normally elicit thus contributing to the immunological education of the host.

Prebiotics

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the probiotic strains may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders especially those with an immunological involvement. Such combinations may be administered in a single formulation or as separate formulations administered at the same or different times and using the same or different routes of administration.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), propellants(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in a mixture with excipients, or in the form of elixirs, solutions or suspensions containing flavouring or colouring agents, or they can be injected parenterally, for example, intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Intranasal administration can be accomplished using a nasal spray, nasal wash solution or direct application within the nose.

Administration to the lung could be in the form of a dry powder, inhaled using an inhaler device. In some cases the formulation is in the form of an aerosol. The aerosol may be a solution, suspension, spray, mist, vapour, droplets, particles, or a dry powder, for example, using a method dose inhaler including HFA propellant, a metered dose inhaler with non-HFA propellant, a nebulizer, a pressurized can, of a continuous sprayer.

The formulation may be designed to encapsulate, remove and/or inactivate a virus. The formulation alternatively or additionally may deter a virus from further infecting the respiratory tract.

To aid delivery to and maintenance in the respiratory tract such as in the nasal cavity, the formulation may have a desired viscosity of 1 centipoise to 2,000 centipoise, for example, 5 cps to 500 cps, or 5 cps to 300 cps. Any suitable viscosity modifying agent may be used to achieve the desired viscosity. Such agents may be suitable natural or synthetic polymeric materials such as hydroxypropyl methylcellulose.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestible solution, or parenterally in which the composition is formulated by an injectable form, for delivery by, for example, an intravenous, intramuscular or subcutaneous route. Alternatively, the formulation may be designed to be delivered by both routes.

The invention is not limited to the embodiments hereinbefore described which may be varied in detail.

REFERENCES

Bouhnik, Y, Survie et effets chez l'homme des bactéries ingérées dans les laits fermentés. Lait 1993, 73; 241-247.

Yang J W, Fan L C, Miao X Y, Mao B, Li M H, Lu H W, Liang S, Xu J F. Corticosteroids for the treatment of human infection with influenza virus: a systematic review and meta-analysis. Clin Microbiol Infect. 2015 October; 21(10):956-63.

Davidson S, Crotta S, McCabe T M, Wack A. Pathogenic potential of interferon αβ in acute influenza infection. Nat Commun. 2014 May 21; 5:3864.

Nakamura S, Davis K M, Weiser J N. Synergistic stimulation of type I interferons during influenza virus coinfection promotes *Streptococcus pneumoniae* colonization in mice. J Clin Invest 2011; 121:3657-65.

Shahangian A, Chow E K, Tian X. et al. Type I IFNs mediate development of postinfluenza bacterial pneumonia in mice. J Clin Invest 2009; 119:1910-20.

Li W, Moltedo B, Moran T M. Type I interferon induction during influenza virus infection increases susceptibility to secondary *Streptococcus pneumoniae* infection by negative regulation of gammadelta T cells. J Virol 2012; 86:12304-12.

Hewitt R, Fame H, Ritchie A, Luke E, Johnston S L, Mallia P. The role of viral infections in exacerbations of chronic obstructive pulmonary disease and asthma. Ther Adv Respir Dis. 2016 April; 10(2):158-74. doi: 10.1177/1753465815618113.

Galani I E, Triantafyllia V, Eleminiadou E E, Koltsida O, Stavropoulos A, Manioudaki M, Thanos D, Doyle S E, Kotenko S V, Thanopoulou K, Andreakos E. Interferon-λ Mediates Non-redundant Front-Line Antiviral Protection against Influenza Virus Infection without Compromising Host Fitness. Immunity. 2017 May 16; 46(5):875-890.

Davidson S, McCabe T M, Crotta S, Gad H H, Hessel E M, Beinke S, Hartmann R, Wack A. IFN-λ is a potent anti-influenza therapeutic without the inflammatory side effects of IFN-α treatment. EMBO Mol Med. 2016 Sep. 1; 8(9):1099-112.

Thiel, S, and Reid K. 1989—Structures and functions associated with the group of mammalian lectins containing collagen-like sequences. FEBS Lett. 250:78.2.

Sastry, K, and Ezekowitz R. A. 1993. Collectins: pattern recognition molecules involved in first line host defense. Curr. Opin. Immunol. 5:59.

Shi X, Zhou W, Huang H, Zhu H, Zhou P, Zhu H, Ju D. Inhibition of the inflammatory cytokine tumor necrosis factor-alpha with etanercept provides protection against lethal H1N1 influenza infection in mice. Crit. Care, 2013; 17(6); R301.

Bartlett N W I, Singanayagam A, Johnston S L. Mouse models of rhinovirus infection and airways disease. Methods Mol Biol. 2015; 1221:181-8. doi: 10.1007/978-1-4939-1571-2_14.

Ivashkiv L B, and Donlin L T. Regulation of type I interferon responses. Nat Rev Immunol. 2014 January; 14(1): 36-49.

Lazear H M, Nice T J, Diamond M S. Interferon-λ: Immune Functions at Barrier Surfaces and Beyond. Immunity, 2015 Jul. 21; 43(1): 15-28.

Wack A, Terczynska-Fyla E, Hartmann R. Guarding the frontiers: the biology of the type III interferons. Nat Immunol. 2015 August; 16(8): 802-9.

Durbin R K, Kotenko S V, Durbin J E. Interferon induction and function at the muscol surface. Immunol Rev. 2013 September; 255(1): 25-39.

Mendoza J L, Schneider W M, Hoffmann H H, Vercauteren K, Jude K M, Xiong A, Moraga I, Horton T M, Glenn J S, de Jong Y P, Rice C M, Garcia K C. The IFN-λ-IFN-λR1-IL-10Rβ Complex Reveals Structural Features Underlying Type III IFN Functional Plasticity. Immunity. 2017 Mar. 21; 46(3): 379-392.

Ichikawa A, Kuba K, Morita M, Chida S, Tezuka H, Hara H, Sasaki T, Ohteki T, Ranieri V M, dos Santos C C, Kawaoka Y, Akira S, Luster A D, Lu B, Penninger J M, Uhlig S, Slutsky A S, Imai Y. CXCL10-CXCR3 enhances the development of neutrophil-mediated fulminant lung injury of viral and nonviral origin. Am J Respir Crit Care Med. 2013 Jan. 1; 187(1):65-77.

Wei Wang, Penghui Yang, et al. Monoclonal antibody against CXCL-10/IP-10 ameliorates influenza A (H1N1) virus induced acute lung injury. Cell Research (2013) 23:577-580.

Hartshorn K L, White M R, Shepherd V, Reid K, Jensenius J C, Crouch E C. Mechanisms of anti-influenza activity of surfactant proteins A and D: comparison with serum collectins. Am J Physiol 1997; 273: L1156-L1166.

Reading P C, Morey L S, Crouch E C, Anders E M. Collectin-mediated antiviral host defense of the lung: evidence from influenza virus infection of mice. J Virol 1997; 71: 8204-8212.

Hartshorn K L, White M R, Voelker D R, Coburn J, Zaner K, Crouch E C. Mechanism of binding of surfactant protein D to influenza A viruses: importance of binding to haemagglutinin to antiviral activity. Biochem J 2000; 351 (Pt 2): 449-458.

Tecle T, White M R, Crouch E C, Hartshorn K L. Inhibition of influenza viral neuraminidase activity by collectins. Arch Virol 2007; 152: 1731-1742.

LeVine A M, Whitsett J A., Hartshorn K L., Crouch E C., Korfhagen T R. S P-D enhances clearance of influenza A virus from the lung in in vivo mouse models. J Immunol 2001; 167:5868-5873.

Vigerust D J, Ulett K B, Boyd K L, Madsen J, Hawgood S, McCullers J A. N-linked glycosylation attenuates H3N2 influenza viruses. J Virol 2007; 81:8593-8600.

Hawgood S, Brown C, Edmondson J, Stumbaugh A, Allen L, Goerke J. et al. Pulmonary collectins modulate strain-specific influenza a virus infection and host responses. J Virol 2004; 30 78: 8565-8572.

LeVine A M (1), Elliott J, Whitsett J A, Srikiatkhachorn A, Crouch E, DeSilva N, Korfhagen T. Surfactant protein-d enhances phagocytosis and pulmonary clearance of respiratory syncytial virus. Am J Respir Cell Mol Biol. 2004 August; 31(2):193-9.

Rich H, Robinson K E, McHugh K J, Clay M E, Alcorn J F. The role of interferon lambda during influenza, *Staphylococcus aureus* super-infection. J Immunol May 1, 2017, 198(1 Supplement) 77.16.

Jounblat R, Clark H, Eggleton P, Hawgood S, Andrew P W, Kadioglu A. The role of surfactant protein D in the colonisation of the respiratory tract and onset of bacteraemia during pneumococcal pneumonia Respir Res. 2005 Oct. 28; 6:126.

World Health Organisation 2007. Global surveillance, prevention and control of chronic respiratory diseases, a comprehensive approach. (Editors Jean Bousquet and Nikolai Khaltaev).

Jartti T, Gem J E. Role of viral infections in the development and exacerbation of asthma in children. J Allergy Clin Immunol. 2017 October; 140(4):895-906.

Almond M H I, Edwards M R, Barclay W S, Johnston S L. Obesity and susceptibility to severe outcomes following respiratory viral infection. Thorax. 2013 July; 68(7):684-6. doi: 10.1136/thoraxjnl-2012-203009.

Steinke J W, Borish L. Immune Responses in Rhinovirus-Induced Asthma Exacerbations. Curr Allergy Asthma Rep. 2016 November; 16(11):78.

Zhou X, Li Q, Zhou X. Exacerbation of Chronic Obstructive Pulmonary Disease. Cell Biochem Biophys. 2015 November; 73(2):349-55.

The invention claimed is:

1. A formulation for oral consumption by a subject, the formulation comprising a *Bifidobacterium longum* strain having the accession number NCIMB 42020 and an ingestible carrier, wherein the formulation is in the form of a tablet.

2. The formulation of claim 1, wherein the *Bifidobacterium longum* strain is in the form of a biologically pure culture.

3. The formulation of claim 1, wherein the *Bifidobacterium longum* strain is in the form of viable cells, non-viable cells, or both viable cells and non-viable cells.

4. The formulation of claim 1, further comprising a probiotic material other than the *Bifidobacterium longum* strain, a prebiotic material, or both a probiotic material other than the *Bifidobacterium longum* strain and a prebiotic material.

5. The formulation of claim 1, further comprising a protein, a peptide, both a peptide and a protein, a lipid, a carbohydrate, a vitamin, a mineral, a trace element, or a combination thereof.

6. The formulation of claim 5, wherein the protein, the peptide, or both the protein and the peptide, is rich in glutamine or glutamate.

7. The formulation of claim 1, wherein the *Bifidobacterium longum* strain is present in an amount of more than $10^6$ cfu per gram of the formulation.

8. The formulation of claim 1, further comprising an adjuvant, a drug entity, a biological compound, or a combination thereof.

9. A formulation for oral consumption by a subject, the formulation comprising a *Bifidobacterium longum* strain having the accession number NCIMB 42020 and an ingestible carrier, wherein the strain is in the form of a freeze-dried powder or a bacterial broth.

\* \* \* \* \*